United States Patent
Yano

(10) Patent No.: US 8,536,280 B2
(45) Date of Patent: Sep. 17, 2013

(54) STAR POLYMER AND COUPLING AGENT FOR ANIONIC POLYMERIZATION

(75) Inventor: Katsuhiko Yano, Yokosuka (JP)

(73) Assignee: Toho Chemical Industry Co., Ltd., Tokyo (JP)

( * ) Notice: Subject to any disclaimer, the term of this patent is extended or adjusted under 35 U.S.C. 154(b) by 1033 days.

(21) Appl. No.: 12/461,861

(22) Filed: Aug. 26, 2009

(65) Prior Publication Data

US 2010/0056748 A1    Mar. 4, 2010

(30) Foreign Application Priority Data

| Aug. 27, 2008 | (JP) | 2008-218580 |
| Feb. 20, 2009 | (JP) | 2009-038489 |
| Aug. 10, 2009 | (JP) | 2009-185711 |

(51) Int. Cl.
  *C08G 65/38* (2006.01)
  *C07C 43/11* (2006.01)

(52) U.S. Cl.
  USPC .......... 525/333.3; 528/212; 568/676

(58) Field of Classification Search
  USPC .......... 525/333.3; 528/212; 568/676
  See application file for complete search history.

(56) References Cited

U.S. PATENT DOCUMENTS

2006/0014913 A1 *  1/2006  Lee et al. .......... 526/266
2007/0224538 A1 *  9/2007  Hada et al. .......... 430/270.1

FOREIGN PATENT DOCUMENTS

JP      2008065266 A  *  3/2008

* cited by examiner

*Primary Examiner* — Ling Choi
*Assistant Examiner* — Chun-Cheng Wang
(74) *Attorney, Agent, or Firm* — Oliff & Berridge, PLC

(57) ABSTRACT

[PROBLEM] To provide a novel star polymer useful as resist materials with high sensitivity and high resolution, and a novel coupling agent for anionic polymerization for synthesizing the polymer.

[MEANS FOR SOLVING THE PROBLEM] A star polymer comprising: a core part derived from a coupling agent for anionic polymerization composed of an acid-degradable compound having an organic group derived from a halide; and an arm part that is attached to the core part and composed of an acid-degradable polymer chain obtained by anionic polymerization; and the coupling agent for anionic polymerization.

5 Claims, No Drawings

STAR POLYMER AND COUPLING AGENT FOR ANIONIC POLYMERIZATION

TECHNICAL FIELD

The present invention relates to novel star polymers, and in particular, relates to star polymers including structures having organic groups derived from halides as a core part and repeating units derived from alkenylphenols as an arm part that is attached to the core part.

The star polymers of the present invention are compounds expected to be applied to resist materials for excimer lasers and electron beams.

Furthermore, the present invention relates to coupling agents for anionic polymerization for novel star polymer syntheses.

BACKGROUND ART

Recently, it is required for resist materials to have, as important characteristics, superior forming performance of resist patterns, which become finer year after year. For fulfilling the request, star polymers have been proposed as one of the materials. Typical among them are alkenylphenolic star polymers, and for example, star polymers having divinylbenzene polymers as a core part and p-hydroxystyrene-styrene copolymers, p-hydroxystyrene-butadiene copolymers or the like as an arm part have been disclosed (Patent Document 1).

Furthermore, as an alkenylphenolic star polymer having a core part other than divinylbenzene polymers, (meth)acrylic acid star polymers including polymer chains containing repeating units derived from di(meth)acrylates as a core part, and polymer chains containing repeating units derived from alkenylphenols and repeating units derived from acrylic acid ester derivatives of alicyclic hydrocarbon groups (additional repeating units derived from alkenylphenyls may be contained) as an arm part have been proposed (Patent Document 2).

However, there is much room for improvement in sensitivity and resolution, for example, in techniques for forming resist patterns with the star polymers ever proposed. For example, the star polymers of Patent Document 2 are acid-degradable because their core parts are formed from poly(meth)acrylate derivatives, so that the polymers are expected to have superior sensitivity when used as resist materials, but the polymers still have problems from the viewpoint of resolution, for example.

SUMMARY OF THE INVENTION

Problem to be Solved by the Invention

In view of the above, it is an object of the present invention to provide a novel polymer, and, in particular, to provide a novel star polymer useful as a resist material with high sensitivity and high resolution and a novel coupling agent for anionic polymerization for synthesizing the polymer.

Means for Solving the Problem

The present inventors have carried out intensive studies in order to solve the above-mentioned problem. As a result, the inventors have found that: when not only an arm part of a star polymer but also a core part is acid-degradable and when a compound containing an organic group derived from a halide is employed as a core part such that the molecular weight distribution of acid-degraded polymer is monodisperse, the molecular weight can be remarkably changed by acid derived from a photo-acid generator (PAG) when the polymer is used as a chemically amplified resist material; and the polymer useful as a resist material with high sensitivity and high resolution can be provided. Thus, the present invention has been accomplished.

Specifically, the present invention relates to a star polymer including a structure having a core part derived from a coupling agent for anionic polymerization represented by Formula (1):

[Chemical Formula 1]

(where P represents an a-valent organic group, a represents 2 to 20, X represents a linking group capable of being cleaved by acid and represented by Formulae (2) to (5):

[Chemical Formula 2]

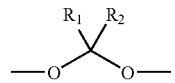

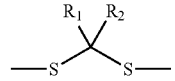

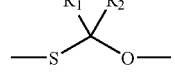

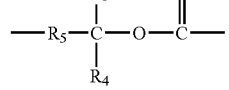

(where each of $R_1$, $R_2$, $R_3$ and $R_4$ independently represents a hydrogen atom; or straight chain, branched or cyclic alkyl group or alkoxy group with 1 to 12 carbon atoms capable of being substituted with an alkoxy group, hydroxy group, halogen atom or epoxy group; aryl group or hydroxy group; and $R_5$ represents a direct bond or straight chain, branched or cyclic alkylene group with 1 to 12 carbon atoms capable of being substituted with an alkoxy group, hydroxy group, halogen atom or epoxy group, or arylene group), Y represents an alkylene group with 1 to 12 carbon atoms or arylene group, and Z represents a halogen atom or epoxy group represented by Formula (6):

[Chemical Formula 3]

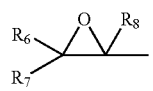

(where each of $R_6$, $R_7$ and $R_8$ independently represents a hydrogen atom or alkyl group with 1 to 12 carbon atoms)); and an arm part that is attached to the core part and composed of a polymer chain obtained by anionic polymerization.

If Z is a bromine atom in Formula (1), it is desirable that Y bonded to Z represents an alkylene group with 1 to 4 carbon atoms.

Furthermore, it is desirable that the arm part composed of the polymer chain obtained by anionic polymerization includes a repeating unit having hydroxystyrene or a derivative thereof.

Furthermore, it is desirable that the arm part composed of the polymer chain obtained by anionic polymerization includes a repeating unit containing an acid-cleavable group, preferably, an acetal-type acid-cleavable group represented by General Formula (p1):

[Chemical Formula 4]

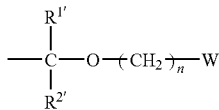
(p1)

(where each of $R^{1'}$ and $R^{2'}$ independently represents a hydrogen atom or alkyl group with 1 to 5 carbon atoms, n represents an integer of 0 to 3, and W represents an alicyclic group or alkyl group with 1 to 5 carbon atoms).

Furthermore, the present invention relates to a coupling agent for anionic polymerization represented by Formula (1).

Effects of the Invention

The star polymers of the present invention have narrow molecular weight distribution and are acid-degradable at their core parts, and degradation sites can be controlled. Therefore, even after acid degradation, the molecular weight distribution becomes monodisperse.

Furthermore, the novel coupling agent for anionic polymerization of the present invention reacts well with a polymer chain as an arm part. Therefore, the star polymer of the present invention can be easily obtained.

In addition, when the star polymers of the present invention are used as chemically amplified resist materials (base resin), the groups represented by Formulae (2) to (5) existing in the core parts of the star polymers of the present invention are cleaved, after an exposure process, by acid generated from a photo-acid generator (PAG) containing the resist. By the cleavage, the molecular weight of the polymers (base resin) significantly changes, and thus, the solubility to a developer also changes significantly. Accordingly, the star polymers of the present invention are expected to be excellent resist materials that achieve high sensitivity and high resolution.

EMBODIMENTS OF THE INVENTION

The present invention relates to a star polymer including a structure having a core part derived from a coupling agent for anionic polymerization represented by Formula (1) and an arm part that is attached to the core part and composed of a polymer chain obtained by anionic polymerization.

Furthermore, the present invention also relates to the coupling agent for anionic polymerization.

Hereinafter, the core part (coupling agent for anionic polymerization) and the arm part in the star polymer of the present invention will be described, respectively.

The core part in the star polymer of the present invention can be derived from a coupling agent for anionic polymerization represented by Formula (1).

[Chemical Formula 5]

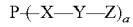
(1)

In Formula (1), P represents an a-valent organic group, a represents 2 to 20, X represents a linking group which can be cleaved by acid, Y represents a straight chain, branched or cyclic alkylene group with 1 to 12 carbon atoms or arylene group, and Z represents a halogen atom or epoxy group represented by Formula (6).

[Chemical Formula 6]

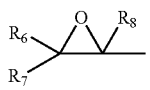
(6)

In Formula (6), each of $R_6$, $R_7$ and $R_8$ independently represents a hydrogen atom or alkyl group with 1 to 12 carbon atoms.

In Formula (1), the organic group represented by P is preferably an organic group with 1 to 20 carbon atoms, more preferably an organic group with 2 to 15 carbon atoms, and specifically preferably an organic group with 3 to 12 carbon atoms.

Examples of the organic group include an aliphatic hydrocarbon group or aromatic hydrocarbon group, and the organic group may include a silicon atom.

The aliphatic hydrocarbon group may be a chain, cyclic group or combination thereof, and may be a saturated or unsaturated group.

Examples of the aromatic hydrocarbon group include a hydrocarbon group having an aromatic hydrocarbon ring, and the aromatic hydrocarbon group may be, for example, an aromatic hydrocarbon ring or a combination of an aromatic hydrocarbon ring and aliphatic hydrocarbon group.

The organic group may have a linking group such as an ether group, polyether group, ester group [—C(=O)—O—], carbonyl group [—C(=O)—], —NH—, —N=, —NH—C (=O)— and —NR$^9$— (R$^9$ is an alkyl group) in the group.

Examples of the alkyl group of R$^9$ include a lower alkyl group with 1 to 5 carbon atoms.

Furthermore, some or all of the hydrogen atoms of the organic group may be substituted with an alkyl group, alkoxy group, halogen atom, hydroxy group or the like.

The alkyl group with which the hydrogen atom of the organic group may be substituted is preferably an alkyl group with 1 to 5 carbon atoms, and a methyl group, ethyl group, propyl group, n-butyl group and tert-butyl group are preferable.

The alkoxy group with which the hydrogen atom of the organic group may be substituted is preferably an alkoxy group with 1 to 5 carbon atoms, more preferably a methoxy group, ethoxy group, n-propoxy group, iso-propoxy group, n-butoxy group and tert-butoxy group, and specifically preferably a methoxy group and ethoxy group.

Examples of the halogen atom with which the hydrogen atom of the organic group may be substituted include a fluorine atom, chlorine atom, bromine atom and iodine atom, and a fluorine atom is preferable.

Specific examples of the organic group of P include groups having structures represented by Formulae below.

[Chemical Formula 7]

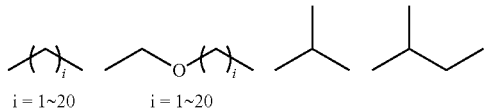

i = 1~20    i = 1~20

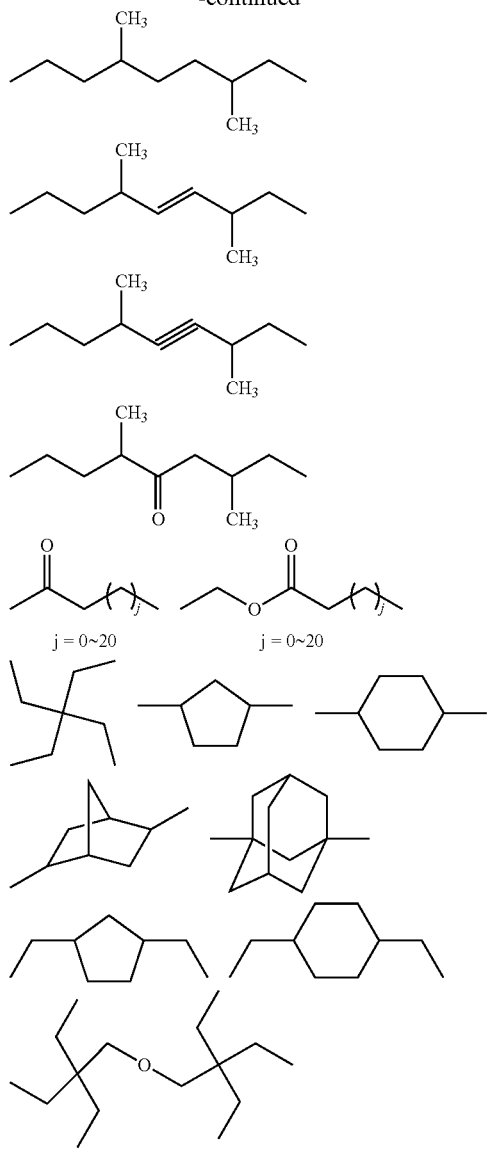
[Chemical Formula 8]
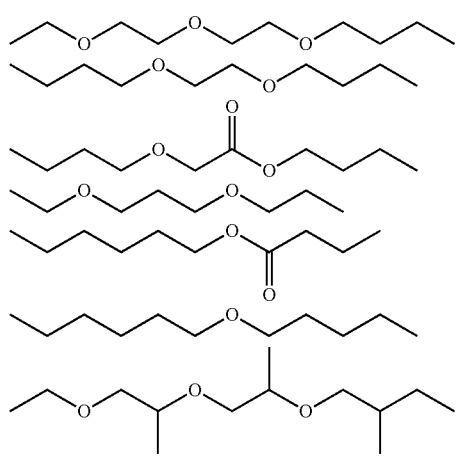
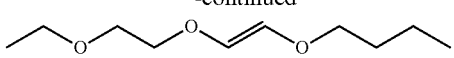
[Chemical Formula 9]
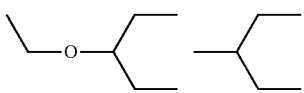
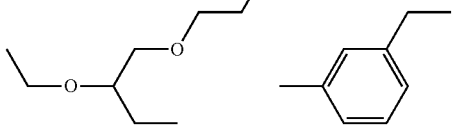
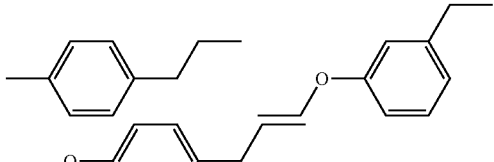
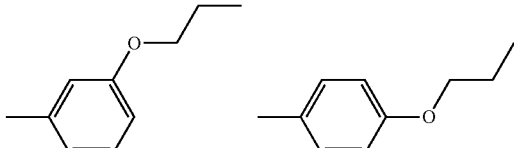
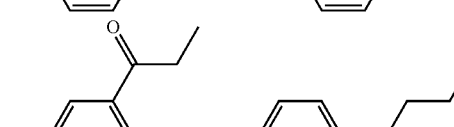
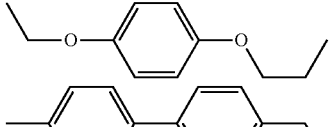
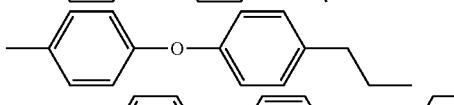
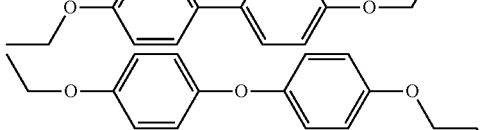
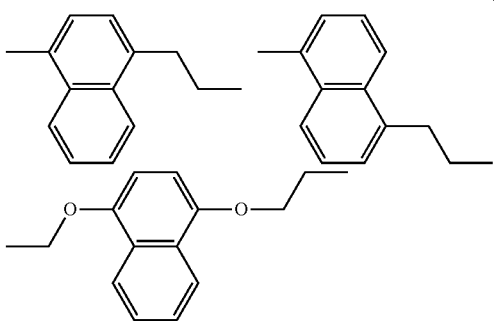

-continued

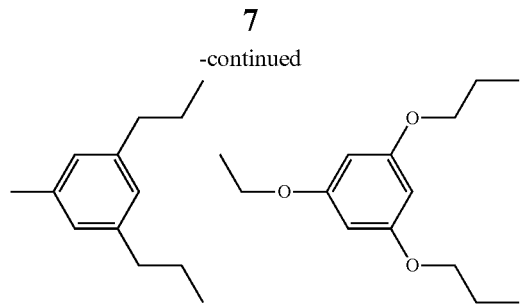

[Chemical Formula 10]

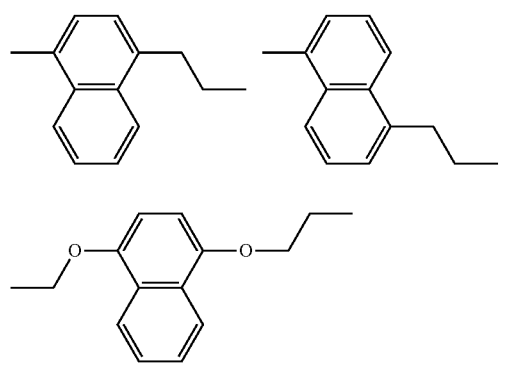

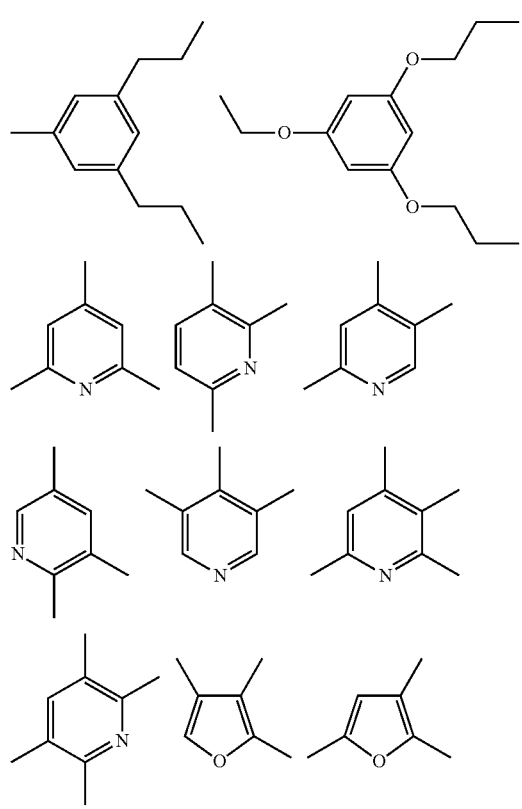

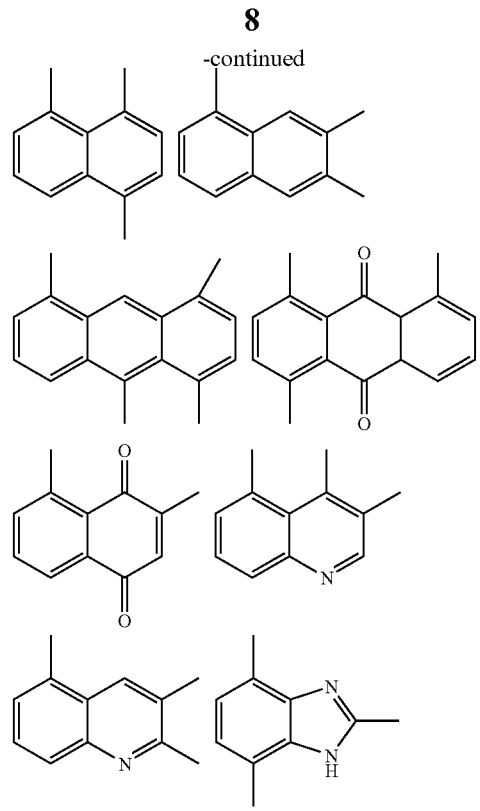

In the coupling agent for anionic polymerization represented by Formula (1), X representing the linking group which can be cleaved by acid is groups represented by Formulae (2) to (5).

Among the linking groups capable of being cleaved and represented by Formulae below, the linking groups represented by Formulae (2) and (4) are preferable, and the linking group represented by Formula (2) is most preferable.

[Chemical Formula 11]

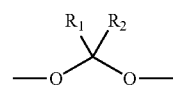 (2)

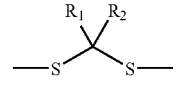 (3)

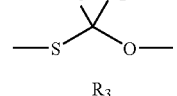 (4)

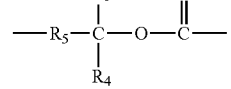 (5)

In Formulae (2) to (5), each of $R_1$, $R_2$, $R_3$ and $R_4$ independently represents a hydrogen atom; straight chain, branched or cyclic alkyl group or alkoxy group with 1 to 12 carbon atoms that may be substituted with an alkoxy group, hydroxy group, halogen atom or epoxy group; aryl group or hydroxy group. $R_5$ represents a direct bond, straight chain, branched or cyclic alkylene group with 1 to 12 carbon atoms that may be substituted with an alkoxy group, hydroxy group, halogen atom or epoxy group, or arylene group.

Examples of the halogen atom of $R_1$ to $R_5$ include a fluorine atom, chlorine atom, bromine atom and iodine atom, and, in particular, a fluorine atom is preferable.

The straight chain, branched or cyclic alkyl group with 1 to 12 carbon atoms is preferably a straight chain or branched alkyl group, and specifically preferably an ethyl group or methyl group. The straight chain, branched or cyclic alkoxy group with 1 to 12 carbon atoms is preferably a straight chain or branched alkoxy group, and specifically preferably an ethoxy group or methoxy group. Furthermore, the straight chain, branched or cyclic alkylene group with 1 to 12 carbon atoms is preferably a straight chain or branched alkylene group, and specifically preferably an ethylene group or methylene group. Moreover, the aryl group is preferably an aryl group with 6 to 20 carbon atoms, and examples of the aryl group include a phenyl group and naphtyl group. Furthermore, the arylene group is preferably an arylene group with 6 to 20 carbon atoms, and examples of the arylene group include a phenylene group and naphthylene group.

Among them, $R_1$, $R_2$, $R_3$ and $R_4$ are preferably a hydrogen atom.

In General Formula (1), Y represents a straight chain, branched or cyclic alkylene group with 1 to 12 carbon atoms or arylene group.

Here, the alkylene group represented by Y is preferably straight or branched.

Furthermore, the number of carbon atoms of the alkylene group is 1 to 12, preferably 1 to 10, more preferably 1 to 5, and specifically preferably 1 or 2 (methylene group or ethylene group), and most preferably all of a pieces of Y are a methylene group or ethylene group.

In the alkylene group, some or all of the hydrogen atoms of the alkylene group may be substituted with substituents (any groups or atoms other than hydrogen atom). Examples of the substituent with which the hydrogen atom of the alkylene group may be substituted include an alkyl group with 1 to 4 carbon atoms, alkoxy group with 1 to 4 carbon atoms and hydroxy group.

Furthermore, the arylene group represented by Y is not specifically limited, examples of the arylene group include an arylene group with 6 to 20 carbon atoms, and an arylene group with 6 to 10 carbon atoms is desirable because it can be synthesized at low cost.

Specific examples of the arylene group include a phenylene group, biphenylene group, fluorenylene group, naphthylene group (naphthalenylene group), anthracenylene group, phenanthrenylene group or pyrenylene group, and the specifically preferred arylene group is a phenylene group or naphthylene group.

In the arylene group, some or all of the hydrogen atoms of the aromatic hydrocarbon ring may be substituted with substituents (any groups or atoms other than hydrogen atom) such as an alkyl group, alkoxy group, halogen atom, halogenated alkyl group and hydroxy group.

The alkyl group with which the hydrogen atom of the arylene group may be substituted is preferably an alkyl group with 1 to 5 carbon atoms, and specifically preferably a methyl group, ethyl group, propyl group, n-butyl group and tert-butyl group.

The alkoxy group with which the hydrogen atom of the arylene group may be substituted is preferably an alkoxy group with 1 to 5 carbon atoms, more preferably a methoxy group, ethoxy group, n-propoxy group, iso-propoxy group, n-butoxy group and tert-butoxy group, and specifically preferably a methoxy group and ethoxy group.

The halogen atom with which the hydrogen atom of the arylene group may be substituted is preferably a fluorine atom.

Examples of the halogenated alkyl group with which the hydrogen atom of the arylene group may be substituted include a group that is the alkyl group exemplified as the substituent of the arylene group of which some or all the hydrogen atoms are substituted with halogen atoms. Examples of the halogen atom of the halogenated alkyl group include the same halogen atoms exemplified as the substituent of the arylene group. The halogenated alkyl group is specifically preferably a fluorinated alkyl group.

Among the groups mentioned above, Y is more preferably an alkylene group with 1 to 12 carbon atoms, specifically preferably a straight chain alkylene group, and most preferably an alkylene group with 1 or 2 carbon atoms (methylene group or ethylene group).

Furthermore, in Formula (1), the halogen atom represented by Z means a chlorine atom, bromine atom and iodine atom.

If Z represents a chlorine atom, Y bonded to the chlorine atom is desirable to represent a methylene group, and if Z represents a bromine atom, Y bonded to the bromine atom is desirable to represent an alkylene group with 1 to 4 carbon atoms.

Examples of the coupling agent for anionic polymerization represented by Formula (1) include compounds represented by Formula (1-1), and specific examples include the compound represented by (1-1-1) to (1-1-4).

[Chemical Formula 12]

(1-1)

(where Y and Z are the same as the respective definitions in the above)

[Chemical Formula 13]

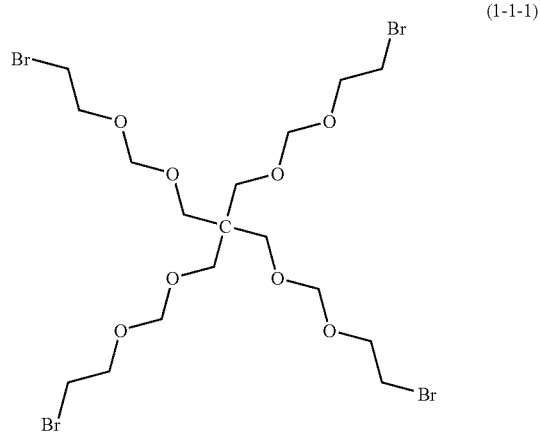

(1-1-1)

[Chemical Formula 14]

(1-1-2)

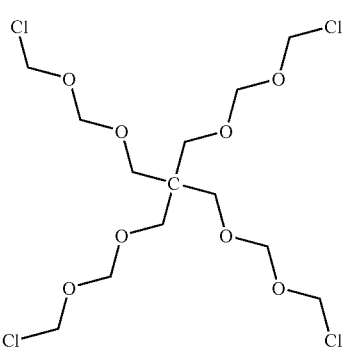

[Chemical Formula 15]

(1-1-3)

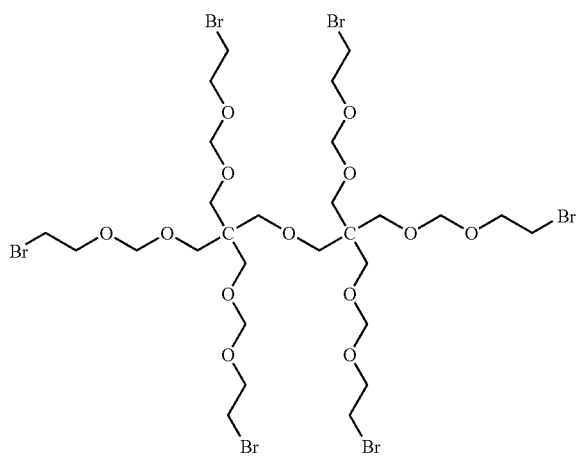

[Chemical Formula 16]

(1-1-4)

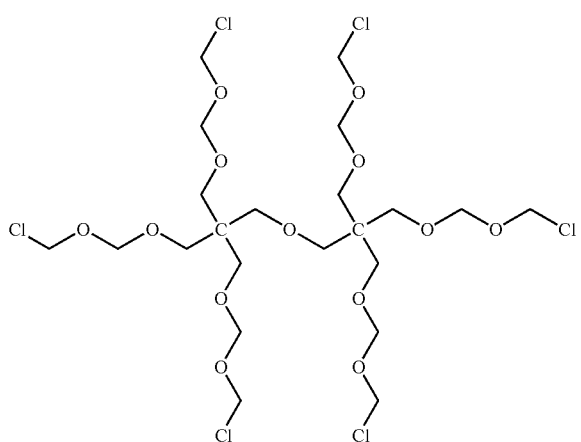

A method for manufacturing the coupling agent for anionic polymerization represented by Formula (1) is not specifically limited.

For example, a multivalent alcohol and a chloromethyl halogenated alkyl ether are reacted to manufacture a coupling agent for anionic polymerization having the bonds of Formula (2).

Furthermore, the star polymer of the present invention is composed of the coupling agent for anionic polymerization represented by Formula (1) (core part) and an arm part composed of a polymer chain obtained by anionic polymerization.

The arm part includes a repeating unit derived from a hydroxystyrene derivative represented by Formula (I).

[Chemical Formula 17]

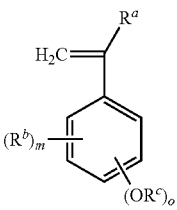
(I)

(where $R^a$ represents a hydrogen atom or alkyl group with 1 to 4 carbon atoms, $R^b$ represents a hydrogen atom, halogen atom or hydrocarbon group with 1 to 12 carbon atoms, and $R^c$ represents a hydrogen atom or protective group. m is an integer of 0 to 4, when m is equal or more than 2, each $R^b$ may be the same or different, m+o is an integer of 1 to 5, and the substitution site is not specifically limited)

In Formula (I), $R^c$ represents a hydrogen atom or protective group.

Here, the protective group is not specifically limited as far as the group is well known in the art as the protective group for a phenolic hydroxy group.

Examples of the protective group include a methoxymethyl group, 2-methoxyethoxymethyl group, bis(2-chloroethoxy)methyl group, tetrahydropyranyl group, 4-methoxytetrahydropyranyl group, tetrahydrofuranyl group, triphenylmethyl group, trimethylsilyl group, 2-(trimethylsilyl)ethoxymethyl group, t-butyldimethylsilyl group, trimethylsilylmethyl group, t-butyl group, t-butoxycarbonyl group, t-butoxycarbonylmethyl group and 2-methyl-2-t-butoxycarbonylmethyl group, and also include substituents shown below:

[Chemical Formula 18]

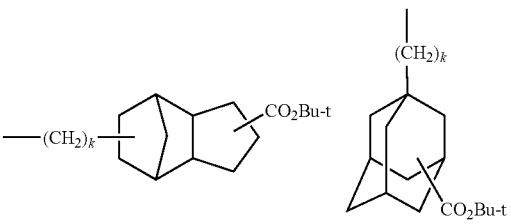

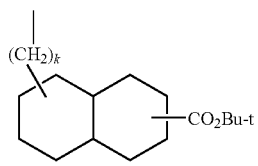

(where k represents 0 or 1). Further examples include groups represented by Formula below:

[Chemical Formula 19]

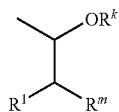

(where $R^k$ represents an unsubstituted or alkoxy-substituted alkyl group with 1 to 20 carbon atoms, cycloalkyl group with 5 to 10 carbon atoms, or unsubstituted or alkoxy-substituted aryl group with 6 to 20 carbon atoms, $R^1$ represents a hydrogen or alkyl group with 1 to 3 carbon atoms, and $R^m$ represents a hydrogen, alkyl group with 1 to 6 carbon atoms or alkoxy group with 1 to 6 carbon atoms).

Specific examples of the substituent are a 1-methoxyethyl group, 1-ethoxyethyl group, 1-methoxypropyl group, 1-methyl-1-methoxyethyl group and 1-(isopropoxy)ethyl group.

Specific examples of the hydroxystyrene derivative represented by Formula (I) include hydroxystyrene derivatives shown below.

[Chemical Formula 20]

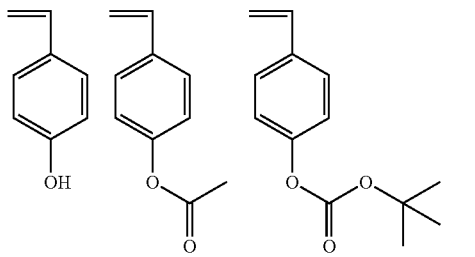

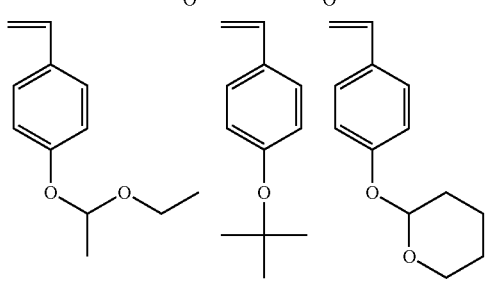

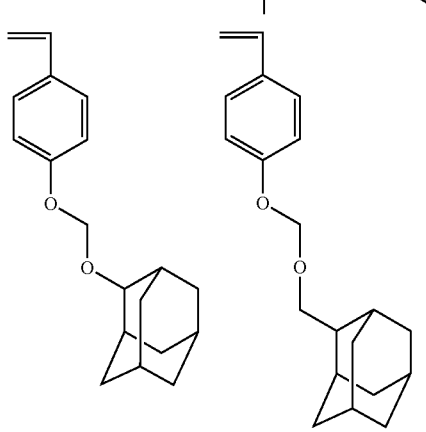

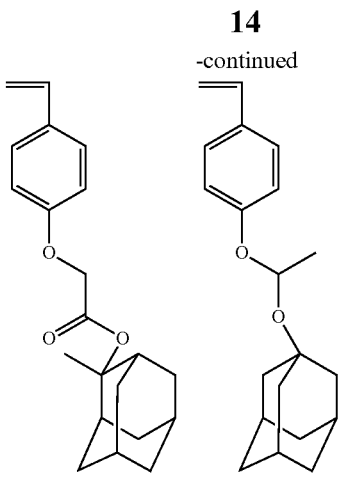

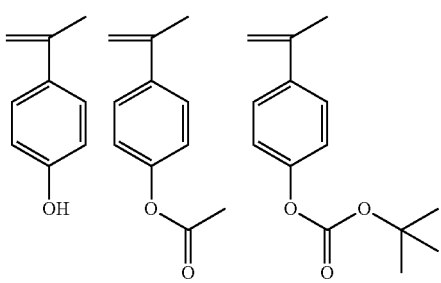

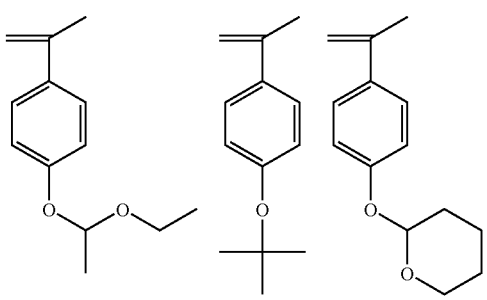

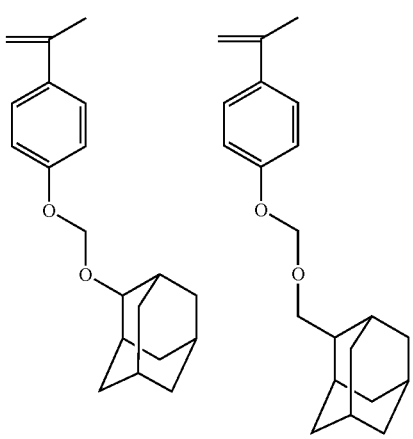

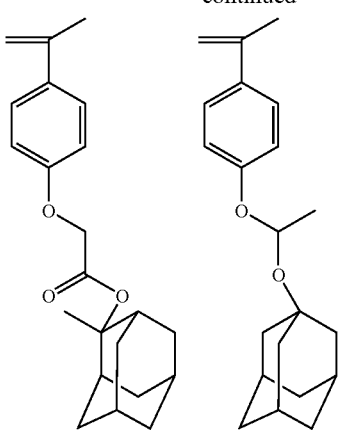

The repeating unit derived from the hydroxystyrene derivative represented by Formula (I) means a repeating unit represented by Formula (I-1):

[Chemical Formula 21]

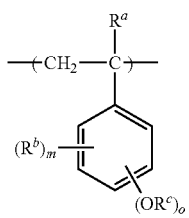

(I-1)

(where $R^a$, $R^b$, $R^c$, m and o are the same as the respective definitions in the above).

Furthermore, the arm part may include a repeating unit derived from a styrene derivative represented by Formula (II), a repeating unit derived from a vinylbenzoic acid derivative represented by Formula (III) and/or a repeating unit derived from an acrylate derivative represented by Formula (IV) in addition to the repeating unit derived from the hydroxystyrene derivative represented by Formula (I).

[Chemical Formula 22]

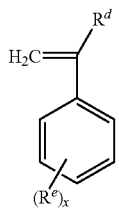

(II)

(where $R^d$ represents a hydrogen atom or alkyl group with 1 to 4 carbon atoms, $R^e$ represents a halogen atom, hydrogen atom or alkyl group with 1 to 6 carbon atoms, x represents an integer of 0 to 5, when x is equal or more than 2, each $R^e$ may be the same or different, and the substitution site is not specifically limited)

[Chemical Formula 23]

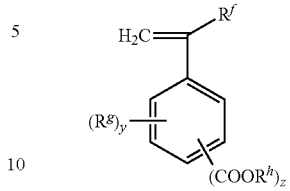

(III)

(where $R^f$ represents a hydrogen atom or alkyl group with 1 to 4 carbon atoms, $R^g$ represents a halogen atom or hydrocarbon group with 1 to 12 carbon atoms, and $R^h$ represents a hydrogen atom or protective group. y is an integer of 0 to 4, when y is equal or more than 2, each $R^g$ may be the same or different, y+z is an integer of 1 to 5, and the substitution site is not specifically limited)

In Formula (III), the protective group represented by $R^h$ is not specifically limited as far as the group is well known in the art as the protective group for a carboxyl group.

Examples of the protective group include a methoxymethyl group, 2-methoxyethoxymethyl group, bis(2-chloroethoxy) methyl group, tetrahydropyranyl group, 4-methoxytetrahydropyranyl group, tetrahydrofuranyl group, triphenylmethyl group, trimethylsilyl group, 2-(trimethylsilyl)ethoxymethyl group, t-butyldimethylsilyl group, trimethylsilylmethyl group, t-butyl group, t-butoxycarbonyl group, t-butoxycarbonylmethyl group and 2-methyl-2-t-butoxycarbonylmethyl group, and also include substituents shown below:

[Chemical Formula 24]

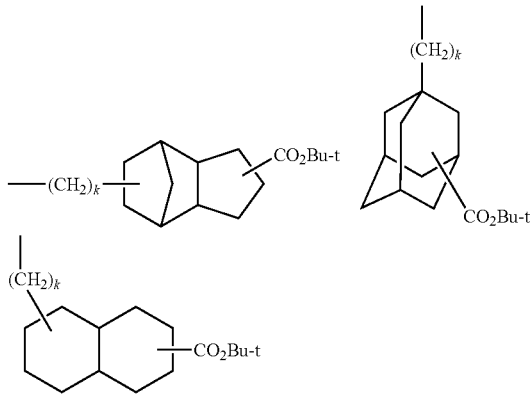

(where k represents 0 or 1). Further examples include groups represented by Formula below:

[Chemical Formula 25]

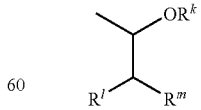

(where $R^k$ represents an unsubstituted or alkoxy-substituted alkyl group with 1 to 20 carbon atoms, cycloalkyl group with 5 to 10 carbon atoms, or unsubstituted or alkoxy-substituted aryl group with 6 to 20 carbon atoms, $R^l$ represents a hydrogen or alkyl group with 1 to 3 carbon atoms, and $R^m$ represents a hydrogen, alkyl group with 1 to 6 carbon atoms or alkoxy group with 1 to 6 carbon atoms).

Specific examples of the substituent include a 1-methoxyethyl group, 1-ethoxyethyl group, 1-methoxypropyl group, 1-methyl-1-methoxyethyl group and 1-(isopropoxy)ethyl group.

[Chemical Formula 26]

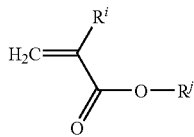
(IV)

(where $R^i$ is a hydrogen atom or alkyl group with 1 to 4 carbon atoms, and $R^j$ represents a hydrogen atom, alkyl group with 1 to 12 carbon atoms, hydrocarbon group having an alicyclic skeleton with 3 or more carbon atoms capable of having a substituent (where the carbon number does not include that of a substituent), alkyl group or hetero group having the hydrocarbon group with an alicyclic skeleton)

The repeating unit derived from a styrene derivative represented by Formula (II) means a repeating unit represented by Formula (II-1), the repeating unit derived from a vinylbenzoic acid derivative represented by Formula (III) means a repeating unit represented by Formula (III-1), and the repeating unit derived from an acrylate derivative represented by Formula (IV) means a repeating unit represented by Formula (IV-1).

[Chemical Formula 27]

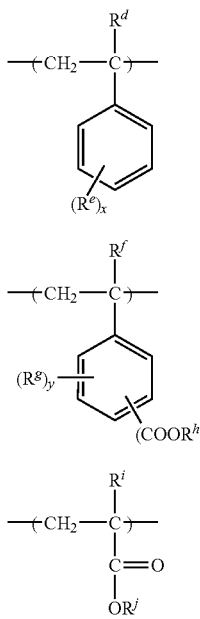

(II-1)

(III-1)

(IV-1)

(where $R^d$ to $R^j$ and x to z are the same as the respective definitions in the above)

In Formulae (II) and (II-1), $R^d$ is preferably a hydrogen atom or methyl group.

Furthermore, in Formulae (II) and (II-1), specific examples of the group represented by $R^e$ include a methyl group, ethyl group, isopropyl group and t-butyl group.

x is preferably 0.

In Formulae (III) and (III-1), $R^f$ is preferably a hydrogen atom or methyl group.

Furthermore, in Formulae (III) and (III-1), specific examples of the group represented by $R^g$ include a methyl group, ethyl group, isopropyl group and t-butyl group.

In Formulae (IV) and (IV-1), $R^i$ is preferably a hydrogen atom or methyl group.

Furthermore, in Formulae (IV) and (IV-1), specific examples of the group represented by $R^j$ include a hydrogen atom, methyl group, ethyl group, n-propyl group, isopropyl group, n-butyl group, t-butyl group, methoxymethyl group, 2-methoxyethoxymethyl group, bis(2-chloroethoxy)methyl group, tetrahydropyranyl group, 4-methoxytetrahydropyranyl group, tetrahydrofuranyl group, triphenylmethyl group, trimethylsilyl group, 2-(trimethylsilyl)ethoxymethyl group, t-butyldimethylsilyl group and trimethylsilylmethyl group.

Furthermore, specific exampleof the alicyclic skeleton include skeletons shown below.

[Chemical Formula 28]

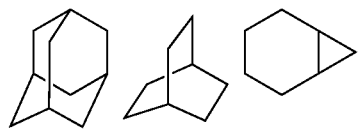

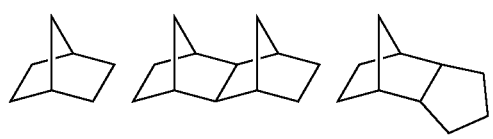

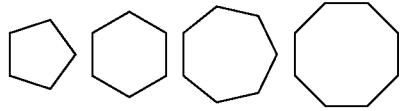

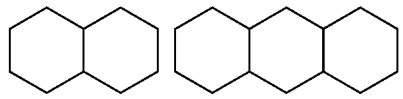

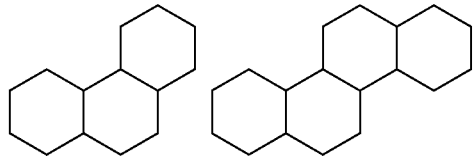

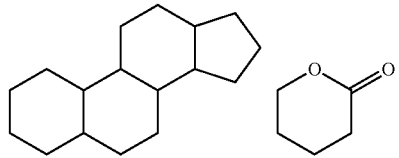

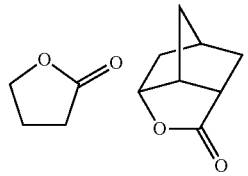

Most preferred examples of $R^j$ include, in particular, a 2-substituted adamantyl group represented by Formula (V):

[Chemical Formula 29]

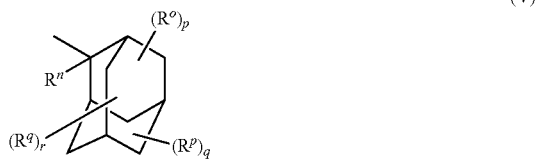

(V)

(where $R''$ represents a hydrogen atom or alkyl group capable of having a substituent, and each of $R^o$ to $R^q$ independently represents a group selected from a group consisting of a hydroxy group, halogen atom, carboxyl group, alkyl group with 1 to 6 carbon atoms, cycloalkyl group with 3 to 8 carbon atoms, alkenyl group with 2 to 7 carbon atoms, alkoxy group, alkoxycarbonyl group and acyl group. Each of p, q and r is independently selected from 0 and an integer of 1 to 3, and when p, q or r is equal to or more than 2, each $R^o$, each $R^p$ and each $R^q$ may be the same or different, respectively).

The arm part of the star polymer of the present invention may include a repeating unit derived from other acrylates shown below as necessary beside the repeating unit derived from an acrylate derivative represented by Formula (IV).

[Acrylic Acid Esters]

methyl acrylate, ethyl acrylate, propyl acrylate, t-butyl acrylate, amyl acrylate, cyclohexyl acrylate, ethylhexyl acrylate, octyl acrylate, t-octyl acrylate, chloroethyl acrylate, 2-ethoxyethyl acrylate, 2,2-dimethyl-3-ethoxypropyl acrylate, 5-ethoxypentyl acrylate, 1-methoxyethyl acrylate, 1-ethoxyethyl acrylate, 1-methoxypropyl acrylate, 1-methyl-1-methoxyethyl acrylate, 1-(isopropoxy)ethyl acrylate, benzyl acrylate, methoxybenzyl acrylate, furfuryl acrylate, tetrahydrofurfuryl acrylate and the like;

[Methacrylic Acid Esters]

methyl methacrylate, ethyl methacrylate, propyl methacrylate, isopropyl methacrylate, amyl methacrylate, t-butyl methacrylate, hexyl methacrylate, cyclohexyl methacrylate, benzyl methacrylate, chlorobenzyl methacrylate, octyl methacrylate, 2-ethoxyethyl methacrylate, 4-methoxybutyl methacrylate, 5-methoxypentyl methacrylate, 2,2-dimethyl-3-ethoxypropyl methacrylate, 1-methoxyethyl methacrylate, 1-ethoxyethyl methacrylate, 1-methoxypropyl methacrylate, 1-methyl-1-methoxyethyl methacrylate, 1-(isopropoxy)ethyl methacrylate, furfuryl methacrylate, tetrahydrofurfuryl methacrylate and the like;

[Crotonic Acid Esters]

methyl crotonate, ethyl crotonate, propyl crotonate, amyl crotonate, cyclohexyl crotonate, ethylhexyl crotonate, octyl crotonate, t-octyl crotonate, chloroethyl crotonate, 2-ethoxyethyl crotonate, 2,2-dimethyl-3-ethoxypropyl crotonate, 5-ethoxypentyl crotonate, 1-methoxyethyl crotonate, 1-ethoxyethyl crotonate, 1-methoxypropyl crotonate, 1-methyl-1-methoxyethyl crotonate, 1-(isopropoxy)ethyl crotonate, benzyl crotonate, methoxybenzyl crotonate, furfuryl crotonate, tetrahydrofurfuryl crotonate and the like; and

[Itaconic Acid Esters]

dimethyl itaconate, diethyl itaconate, dipropyl itaconate, diamyl itaconate, dicyclohexyl itaconate, bis(ethylhexyl)itaconate, dioctyl itaconate, di-t-octyl itaconate, bis(chloroethyl)itaconate, bis(2-ethoxyethyl)itaconate, bis(2,2-dimethyl-3-ethoxypropyl)itaconate, bis(5-ethoxypentyl)itaconate, bis(1-methoxyethyl)itaconate, bis(1-ethoxyethyl)itaconate, bis(1-methoxypropyl)itaconate, bis(1-methyl-1-methoxyethyl)itaconate, bis(1-(isopropoxy)ethyl)itaconate, dibenzyl itaconate, bis(methoxybenzyl)itaconate, difurfuryl itaconate, ditetrahydrofurfuryl itaconate and the like.

Among the other acrylates, in particular, preferred examples include acrylates or methacrylates having an alkyl group with a tertiary carbon at the α-oxygen of an ester such as t-butyl acrylate, t-butyl methacrylate, 1,1-dimethylpropyl acrylate and 1,1-dimethyl methacrylate.

As described above, the arm part of the star polymer of the present invention may include a repeating unit derived from the hydroxystyrene derivative represented by Formula (I), and may further include a repeating unit derived from the styrene derivative represented by Formula (II), repeating unit derived from the vinylbenzoic acid derivative represented by Formula (III), repeating unit derived from the acrylate derivative represented by Formula (IV) and/or repeating unit derived from the other acrylates.

In addition, in the arm part of the star polymer of the present invention, preferably, the repeating unit is desirable to include an acid-cleavable group.

Here, "acid-cleavable" means that a group can be cleaved by acid from a polymer chain contained in the arm part of the star polymer of the present invention. In addition, the acid-cleavable group also has a character to make the whole polymer alkali insoluble before cleavage to inhibit the dissolution. That is, the whole polymer is alkali insoluble before acid reaction, but an acid-cleavable group is cleaved from a polymer chain by acid, so that the whole polymer becomes alkali soluble.

As for the "acid-cleavable group", generally, a group forming a cyclic or chain tertiary alkyl ester together with the carboxy group of (meth)acrylic acid and the like (hereinafter, referred to as a tertiary alkyl ester-type acid-cleavable group), acetal-type acid-cleavable group such as an alkoxyalkyl group, and the like are widely known.

[Tertiary Alkyl Ester-Type Acid-Cleavable Group]

Here, the "tertiary alkyl ester (group)" means a structure in which the hydrogen atom of a carboxy group in (meth)acrylic acid and the like is substituted with a chain or cyclic alkyl group to form an ester, that is, a tertiary carbon atom of a chain or cyclic alkyl group is bonded to the end oxygen atom of a carbonyloxy group (—C(O)—O—). In the tertiary alkyl ester, the bond between the oxygen atom and the tertiary carbon atom is cleaved by acid.

Examples of the tertiary alkyl ester-type acid-cleavable group include an aliphatic branched acid-cleavable group and acid-cleavable group containing an alicyclic group.

The aliphatic branched acid-cleavable group is preferably a tertiary alkyl group with 4 to 8 carbon atoms bonded to the end oxygen atom of a carbonyloxy group (—C(O)—O—) of (meth)acrylic acid and the like, and examples of the tertiary alkyl group include a tert-butyl group, tert-pentyl group, and tert-heptyl group.

Examples of the acid-cleavable group containing an alicyclic group include a group having tertiary carbon atom on the ring skeleton of an cyclic alkyl group bonded to the end oxygen atom of the carbonyloxy group (—C(O)—O—) of (meth)acrylic acid and the like.

Here, examples of the cyclic alkyl group include a polycycloalkyl group such as a monocycloalkyl group, bicycloalkyl group, tricycloalkyl group and tetracycloalkyl group which may be substituted with a lower alkyl group, fluorine atom or fluorinated alkyl group, and more specific examples include a cyclopentyl group, cyclohexyl group, adamantyl group, norbornyl group, isobornyl group, tricyclodecanyl group and tetracyclododecanyl group.

Accordingly, specific examples of the acid-cleavable group containing an alicyclic group include a 2-methyl-2-adamantyl group and 2-ethyl-2-adamantyl group. Further examples include an alicyclic group such as an adamantyl group, cyclohexyl group, cyclopentyl group, norbornyl group, tricyclodecanyl group and tetracyclododecanyl group to which a branched alkylene group with a tertiary carbon atom is bonded.

A preferred group for the tertiary alkyl ester-type acid-cleavable groups is a group represented by Formula (p0), and a more preferred group is that represented by Formula (p0-1).

[Chemical Formula 30]

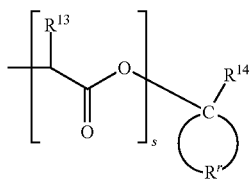

(p0)

[where s is 0 or 1, $R^{13}$ is a hydrogen atom or methyl group, $R^{14}$ is an alkyl group (which can be either a straight chain or branched chain and is preferably an alkyl group with 1 to 5 carbon atoms), and $R^r$ is a group forming an alicyclic group together with the carbon atom to which the $R^r$ is bonded.]

Examples of the alicyclic group containing $R^r$ include the same groups as those exemplified for the <cyclic alkyl group>, and a preferred the alicyclic group containing $R^r$ is a polycyclic alicyclic group.

[Chemical Formula 31]

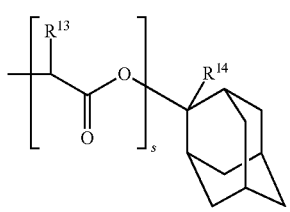

(p0-1)

[where s is 0 or 1, $R^{13}$ is a hydrogen atom or methyl group, and $R^{14}$ is an alkyl group (which can be either a straight chain or branched chain and is preferably an alkyl group with 1 to 5 carbon atoms).]

A more preferred $R^{14}$ has a carbon number of 1 to 3 and a methyl group or ethyl group is more preferable.

[Acetal-Type Acid-Cleavable Group]

The "acetal-type acid-cleavable group" is generally a group which is an alkali soluble group such as a carboxy group or hydroxy group of which the end hydrogen atom is substituted and bonded to the oxygen atom. In addition, the bond between the acetal-type acid-cleavable group and the oxygen atom bonded to the acetal-type acid-cleavable group is cleaved by acid.

Examples of the acetal-type acid-cleavable group include a group represented by General Formula (p1).

[Chemical Formula 32]

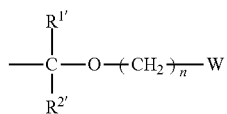

(p1)

In Formula (p1), each of $R^{1'}$ and $R^{2'}$ independently represents a hydrogen atom or alkyl group with 1 to 5 carbon atoms, n represents an integer of 0 to 3, and W represents an alicyclic group or alkyl group with 1 to 5 carbon atoms.

The alkyl group with 1 to 5 carbon atoms of $R^{1'}$, $R^{2'}$ and W in Formula (p1) is preferably a methyl group or ethyl group, and most preferably a methyl group.

Furthermore, examples of the alicyclic group of W include the groups exemplified for the "cyclic alkyl group".

Specific examples of the acetal-type acid-cleavable group represented by Formula (p1) include groups shown below.

[Chemical Formula 33]

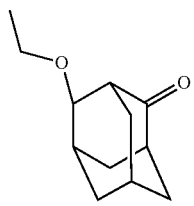

(11)

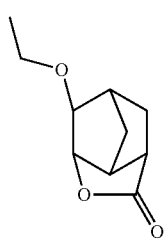

(12)

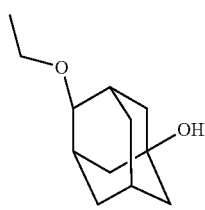

(13)

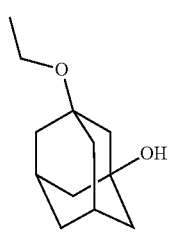

(14)

(15) 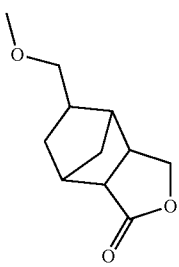

(16) 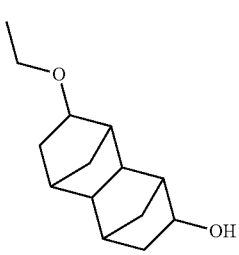

(17) 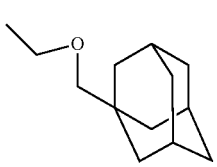

(18) 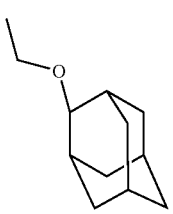

(19) 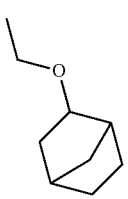

(20) 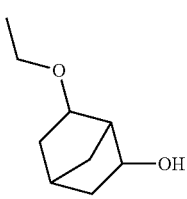

(21) 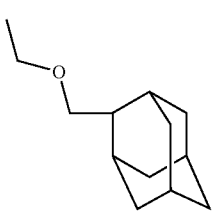

(22) 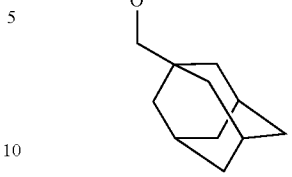

(23)

(24)

Further examples of the acetal-type acid-cleavable group include a group represented by General Formula (p2).

[Chemical Formula 34]

(p2)

In Formula (p2), each of $R^{10}$ and $R^{11}$ independently represents a hydrogen atom or straight chain or branched alkyl group, and $R^{12}$ represents a straight chain, branched or cyclic alkyl group. Alternatively, $R^{10}$ and $R^{12}$ may be bonded to form a ring.

The straight chain or branched alkyl group of $R^{10}$ and $R^{11}$ is preferably a straight chain or branched alkyl group with 1 to 15 carbon atoms, an ethyl group and methyl group are preferred, and a methyl group is most preferred. In particular, it is preferable that one of $R^{10}$ and $R^{11}$ is a hydrogen atom and the other is a methyl group.

The straight chain, branched or cyclic alkyl group of $R^{12}$ is preferably a straight chain, branched or cyclic alkyl group with 1 to 15 carbon atoms. The straight chain or branched alkyl group is preferably a straight chain or branched alkyl group with 1 to 5 carbon atoms, more preferably an ethyl group and methyl group, and in particular, most preferably an ethyl group. Furthermore, the desirable cyclic alkyl group is a cyclic alkyl group with 4 to 15 carbon atoms, preferably a cyclic alkyl group with 4 to 12 carbon atoms, and more preferably a cyclic alkyl group with 5 to 10 carbon atoms. Specific examples include a polycycloalkyl group such as a monocycloalkyl group, bicycloalkyl group, tricycloalkyl group or tetracycloalkyl group which may be substituted with a fluorine atom or fluorinated alkyl group, more specific examples include a cyclopentyl group, cyclohexyl group, adamantyl group, norbornyl group, isobornyl group, tricyclodecanyl group and tetracyclododecanyl group, and among them an adamantyl group is most desirable.

Furthermore, when $R^{10}$ and $R^{12}$ are bonded to form a ring in Formula (p2), a desirable ring is a 4- to 7-membered ring, preferably a 4- to 6-membered ring, and specifically, it is preferable that a tetrahydropyranyl group, tetrahydrofuranyl group or the like are formed.

Each ratio of the repeating units in the arm part of the star polymer of the present invention can be optionally selected in accordance with each ratio of monomers used for a reaction.

For example, the content of a repeating unit derived from the hydroxystyrene derivative represented by Formula (I) is 1 to 100 mol % in all repeating units of an arm part, preferably 10 to 100 mol %, and more preferably 30 to 100 mol %.

Furthermore, the content of a repeating unit derived from the styrene derivative represented by Formula (II), that of a repeating unit derived from the vinylbenzoic acid derivative represented by Formula (III) or that of a repeating unit derived from an acrylate derivative represented by Formula (IV) is 0 to 99 mol %, preferably 0 to 90 mol %, and more preferably 0 to 70 mol % in all repeating units of an arm part.

The number average molecular weight Mn of a polymer (arm polymer) chain contained in the arm part of the star polymer of the present invention is preferably a range of 500 to 300,000, more preferably 500 to 100,000, and even more preferably 1,000 to 20,000 by GPC (converted to polystyrene).

Furthermore, at this time, it is desirable that the ratio (Mw/Mn) of the weight average molecular weight (Mw) to the number average molecular weight (Mn) is preferably in a range of 1.01 to 3.00, more preferably in a range of 1.01 to 2.00, and even more preferably in a range of 1.01 to 1.50.

The method for manufacturing the star polymer of the present invention is not specifically limited, but, for example, the following method is desirable because a reaction is easily controlled and a star polymer with a controlled structure can be manufactured: in the presence of an anionic polymerization initiator, a hydroxystyrene derivative represented by Formula (I) is anion-polymerized, if desired, an anionic polymerizable monomer (for example, an acrylate derivative represented by Formula (IV)) is further reacted to form an arm part, then the arm part is reacted with a coupling agent for anionic polymerization represented by Formula (1) for a core part to form a star polymer, and from the obtained copolymer all or some of protective groups of phenolic hydroxy groups and the like are removed.

Examples of the anionic polymerization initiator used for the anionic polymerization include an alkali metal or organic alkali metal, and examples of the alkali metal include lithium, sodium, potassium and cesium.

Examples of the organic alkali metal include alkylated, allylated and arylated compounds of the alkali metals, and specific examples can include ethyllithium, n-butyllithium, s-butyllithium, t-butyllithium, ethylsodium, biphenyllithium, naphthalenelithium, triphenyllithium, naphthalenesodium, α-methylstyrene sodium dianion, 1,1-diphenylhexyllithium and 1,1-diphenyl-3-methylpentyllithium.

The polymerization reaction for synthesizing a polymer of an arm part in the method described above can include either methods in which an anionic polymerization initiator is added dropwise into a monomer (mixed) solution and in which a monomer (mixed) solution is added dropwise into a solution containing an anionic polymerization initiator, but a preferred method is that a monomer (mixed) solution is added dropwise into a solution containing an anionic polymerization initiator because the molecular weight and molecular weight distribution can be controlled.

The polymerization reaction of a polymer of an arm part is generally carried out under an inert gas atmosphere such as nitrogen and argon in an organic solvent at a temperature range of −100 to 50° C., and preferably −100 to 40° C.

Examples of the organic solvent used for the synthesis of an arm polymer include aliphatic hydrocarbons such as n-hexane and n-heptane, alicyclic hydrocarbons such as cyclohexane and cyclopentane, aromatic hydrocarbons such as benzene and toluene, ethers such as diethyl ether, tetrahydrofuran (THF) and dioxane, as well as organic solvents generally used in anionic polymerization such as anisole and hexamethylphosphoramide, and these organic solvents may be used alone or as a mixture of two or more solvents. Among them, toluene, n-hexane and THF can be exemplified as preferred solvents.

When a polymer of the arm part is a copolymer, the copolymer can include any polymeric forms of a random copolymer, partial block copolymer and complete block copolymer. These can be properly synthesized by selection of an adding method of monomers used for polymerization.

A reaction for forming a star polymer by a connection of the arm part obtained in this manner to a core part can be carried out by, after the completion of the polymerization of the arm part, a further addition of a coupling agent for anionic polymerization represented by Formula (1) into the reacted solution.

The reaction is generally carried out under an inert gas atmosphere such as nitrogen or argon in an organic solvent at a temperature of −100° C. to 50° C., and preferably −80° C. to 40° C., to control a structure and to obtain a polymer with a narrow molecular weight distribution.

Furthermore, the polymer forming reaction can be continuously carried out in the solvent used for forming the arm part, and alternatively, carried out in a solvent with another composition by an addition of other solvent, or in another solvent replaced. Examples of the solvent used herein can be the same solvents as those for synthesizing the arm part.

A ratio (Mw/Mn) of the weight average molecular weight (Mw) to the number average molecular weight (Mn) of a polymer formed by the method described above is preferably in a range of 1.01 to 3.00, more preferably in a range of 1.01 to 2.00, and even more preferably in a range of 1.01 to 1.50. The number average molecular weight of a formed polymer is preferably in a range of 1,000 to 1,000,000, more preferably 1,500 to 500,000, even more preferably 1,500 to 50,000, and specifically preferably 2,000 to 20,000.

A reaction for removing a protective group of a phenolic hydroxyl group and the like from the copolymer obtained in this manner is carried out in the presence of the solvents exemplified in the polymerization as well as a solvent or a mixture of two or more solvents of alcohols such as methanol and ethanol, ketones such as acetone and methyl ethyl ketone, multivalent alcohol derivatives such as methyl cellosolve and ethyl cellosolve, water or the like, with an acidic reagent as a catalyst such as hydrochloric acid, sulfuric acid, oxalic acid, hydrogen chloride gas, hydrobromic acid, p-toluenesulfonic acid, 1,1,1-trifluoroacetic acid, or a bisulfate represented by $LiHSO_4$, $NaHSO_4$ or $KHSO_4$, at a temperature of room temperature to 150° C. In the reaction, all or some of the protective groups of phenolic hydroxy groups can be removed by a suitable combination of a type and concentration of a solvent, a type and addition amount of a catalyst, a reaction temperature and a reaction time.

Furthermore, when a repeating unit derived from the acrylate derivative represented by Formula (IV) is included in the arm part of the star polymer of the present invention, the ester group of the repeating unit can be hydrolyzed to derive a carboxyl group. The hydrolysis can be carried out by a method well known in the art, and, for example, can be carried out by acid hydrolysis in a similar condition to the condition described above for removing the protective group. The hydrolysis of an ester group is preferably carried out simultaneously with the removal of a protective group of a phenolic hydroxy group. The star polymer having an acrylic acid-type repeating unit in the molecule obtained in this manner has a high alkali solubility, so that it is particularly preferred for resist materials.

The star polymer of the present invention obtained in the manufacturing method described above can be used without any purification, but if necessary, may be purified. The purification can be carried out by a method generally used in the art, and, for example, by fractional reprecipitation. The fractional reprecipitation is preferably carried out with a mixed solvent of a solvent with a high polymer solubility and that with a low solubility. For example, the star polymer of the present invention is dissolved by heating in a mixed solvent and then cooled, or the star polymer of the present invention is dissolved in a solvent with a high polymer solubility and then the star polymer is precipitated by an addition of a solvent with a low polymer solubility to purify the product.

EXAMPLES

Hereinafter, the present invention will be described in detail with reference to Examples, but the technical scope of the present invention is not unreasonably limited to Examples.

Preparation Example 1

Preparation of Star Polymer (Polymer (A)-1)

Preparation Example 1-1

Synthesis of Coupling Agent for Anionic Polymerization

Under a nitrogen atmosphere, 247.0 g of acetone, 80.2 g of diisopropylethylamine and 80.1 g of 2-chloroethyl chloromethyl ether were added to 13.0 g of pentaerythritol and the whole was held at 30° C. for 4 hours with stirring. Then, ethyl acetate was added to the reaction mixture, the organic phase was washed with an oxalic acid aqueous solution and ion-exchanged water 4 times. The obtained organic phase was concentrated under reduced pressure to obtain 47.4 g of pentaerythritol-tetra(2-chloroethoxymethyl)ether (yield 98%).

Under a nitrogen atmosphere, to 11.2 g of pentaerythritol-tetra(2-chloroethoxymethyl)ether obtained above, 560.0 g of hexamethylphosphoric triamide, 144.7 g of bromoethane and 1.8 g of sodium bromide were added and the whole was held at 80° C. for 24 hours with stirring. Then, the reaction mixture was cooled to room temperature and the reaction mixture was concentrated under reduced pressure. To the obtained concentrated mixture, methyl t-butyl ether was added, and the organic phase was washed with ion-exchanged water 4 times. Then, anhydrous magnesium sulfate was added to the organic phase to dry. After filtration, the filtrate was concentrated under reduced pressure to obtain 12.3 g of pentaerythritol-tetra(2-bromoethoxymethyl)ether as a coupling agent for anionic polymerization (yield 81%).

Preparation Example 1-2

Synthesis of Arm Part (Polymer Chain) and Synthesis of Acid-Degradable Polymer

Under a nitrogen atmosphere, 119.5 g of tetrahydrofuran (hereinafter referred to as THF) was cooled to −60° C. With stirring, 15 millimole of s-butyllithium was added while the temperature was held at −60° C., subsequently 24.5 g of p-ethoxyethoxystyrene (hereinafter referred to as PEES) was added dropwise over 50 minutes, and then the reaction was continued for 1 hour.

At this stage, a small amount of the reacted solution was taken, methanol was added to stop the reaction, and then the reactant was subjected to gel permeation chromatography (hereinafter referred to as GPC) measurement to reveal that the obtained PEES polymer was a monodisperse polymer with Mn=1450 and Mw/Mn=1.20 as converted to polystyrene.

Then, while holding the reaction system at −60° C., 3.2 g of pentaerythritol-tetra(2-bromoethoxymethyl)ether obtained in Preparation Example 1-1 was added dropwise over 10 minutes, and then the reaction was continued for 1 hour.

Then, to the reaction system, methanol was added to stop the reaction. The subsequent GPC measurement of the reactant revealed that the obtained acid-degradable polymer was a monodisperse polymer with Mn=3670 and Mw/Mn=1.24 as converted to polystyrene.

That is, it was observed that the molecular weight of the polymer increased after the reaction with pentaerythritol-tetra(2-bromoethoxymethyl)ether while the monodisperse polymer state before the reaction was held. Accordingly, the polymer was ascertained to be a polymer with a star shape.

Preparation Example 1-3

Hydrolysis of PEES (Removal of Protective Group)

To the polymer solution obtained from Preparation Example 1-2, methyl isobutyl ketone (hereinafter referred to as MIBK) was added, the organic phase was washed with ion-exchanged water twice, then the organic phase was concentrated under reduced pressure to make a MIBK solution with a polymer content of 40% by mass, and isopropyl alcohol (hereinafter referred to as IPA) was further added to make a solution with a polymer content of 20% by mass.

With respect to 100 parts by mass of the solution, 1 part by mass of oxalic acid dihydrate and 2 parts by mass of ion-exchanged water were added and the whole was heated to 50° C. With stirring, the reaction was further continued for 6 hours while the temperature was held at 50° C.

On the reaction, $^{13}$C-NMR spectra of the polymers before and after the reaction were measured and the results were compared. After the reaction, the absorption observed around 117 ppm and derived from the PEES polymer disappeared, and the absorption around 115 ppm derived from the p-hydroxystyrene polymer was newly observed. In addition, the peak observed around 96 ppm and derived from an acetal bond (—O—CH$_2$—O—) was ascertained to be held both before and after the hydrolysis.

Furthermore, GPC measurement of the polymer after the reaction showed Mn=2560 as converted to polystyrene, and no significant change was observed in the peak shapes of GPC between before and after the reaction.

From these results, it was ascertained that hydrolysis progressed at the ethoxyethoxy groups of PEES and an alkenylphenolic polymer with p-hydroxystyrene (hereinafter referred to as PHS) segments as a main skeleton of the arm part was obtained. Furthermore, the —O—CH$_2$—O— bonds introduced to the core part of the polymer was held, and the polymer after the reaction held a star shape.

Preparation Example 1-4

Introduction of Methoxyadamantyl Group

To the polymer solution obtained in Preparation Example 1-3, MIBK was added, and the organic phase was washed with ion-exchanged water three times. Then, the organic phase was concentrated under reduced pressure to make a solution with a polymer content of 50% by mass, and then THF was added to make a solution with a polymer content of 10% by mass.

To 130.5 g of the obtained polymer solution, 2.2 g of 60% sodium hydride was added and the whole was held at room temperature for 30 minutes with stirring. Then, 4.8 g of 2-chloromethoxyadamantane was added dropwise over 5 minutes and the reaction was further continued for 12 hours at room temperature.

To the reaction system, an aqueous solution of oxalic acid was added to stop the reaction, then MIBK was added, and the organic phase was washed with ion-exchanged water three times. Then, the organic phase was concentrated under reduced pressure to be replaced with a solution of propylene glycol monomethyl ether acetate (hereinafter referred to as PGMEA).

$^{13}$C-NMR measurement of the obtained polymer showed novel absorptions around 82 ppm, around 93 ppm and around 116 ppm derived from the unit in which a methoxyadamantyl group was introduced to PHS (hereinafter referred to as PHS-MOAd).

In addition, the ratio of the PHS unit to PHS-MOAd was 75/25.

Furthermore, it was ascertained that the peak around 96 ppm derived from the —O—CH$_2$—O— bond introduced to the core part of the polymer was held.

Furthermore, GPC measurement of the polymer after the reaction showed a monodisperse polymer with Mn=2790 and Mw/Mn=1.30 as converted to polystyrene, and no change was observed in the peak shapes of GPC between before and after the adamantyl group introduction.

From these results, it was ascertained that the alkenylphenolic polymer with PHS/PHS-MOAd segments as a main skeleton of the arm part was obtained, the acetal bonds introduced to the core part of the polymer were held, and the polymer held a star shape.

A structure of the polymer obtained in Preparation Example 1-5 (hereinafter referred to as Polymer (A)-1) is shown below. In Chemical Formula, each sign at lower right of parentheses shows the ratio of each building block to total building blocks contained in a polymer chain as the arm part of Polymer (A)-1 (mol %; composition ratio), and each ratio was calculated from $^{13}$C-NMR.

[Chemical Formula 35]

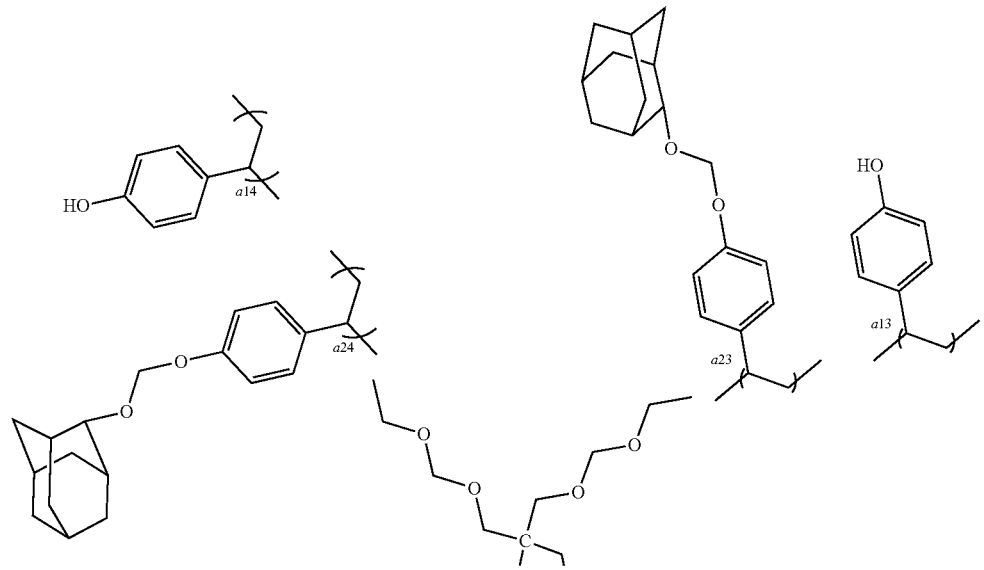

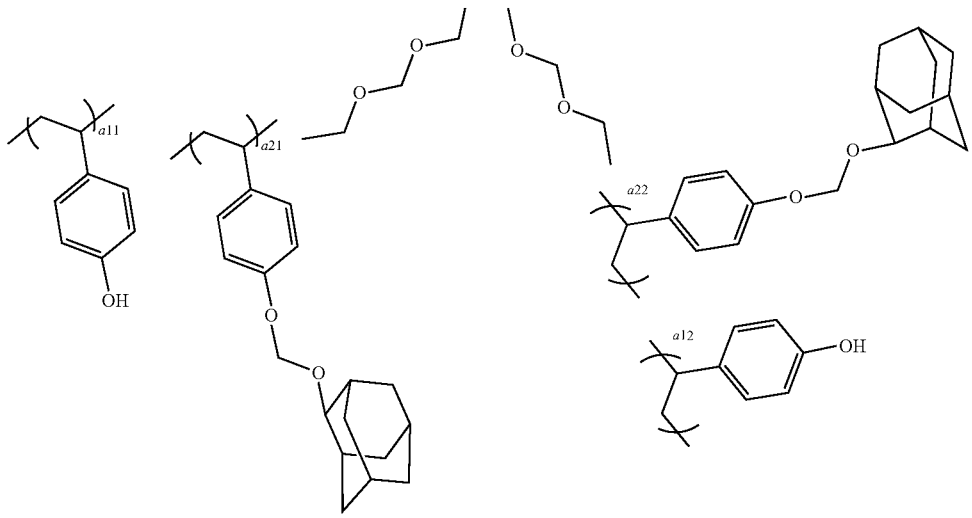

[(a11 + a12 + a13 + a14)/(a21 + a22 + a23 + a24) = 75/25 (molar ratio); Mw = 2790, Mw/Mn = 1.30]

Comparative Preparation Example 1

Preparation of Polymer (A)-2

10 g of poly-4-hydroxystyrene (Mw=4000, Mw/Mn=1.1) was dissolved in 100 ml of THF, to which 0.92 g of 60% sodium hydride was added. To the solution, 4.37 g of 2-chloromethoxyadamantane was added and the whole was stirred at room temperature for 20 hours. After stirring, ion-exchanged water was added to stop the reaction and the solution was concentrated. Then, the reactant was diluted with 400 ml of ion-exchanged water, extracted with 100 ml of ethyl acetate three times, and washed sequentially with hydrochloric acid, a saturated aqueous solution of $NaHCO_3$ and a saturated aqueous solution of NaCl. The obtained solution was concentrated, the reprecipitation was carried out in an ethyl acetate-n-heptane system, and the precipitate was dried to obtain a white solid.

The obtained solid was subjected to GPC measurement to show that Polymer (A)-2 obtained had Mw=4200 and Mw/Mn=1.1 as converted to polystyrene. Furthermore, the composition ratio (molar ratio) was calculated from $^{13}C$-NMR and $^1H$-NMR.

A structure of Polymer (A)-2 obtained from Comparative Preparation Example 1 is as shown below.

[Chemical Formula 36]

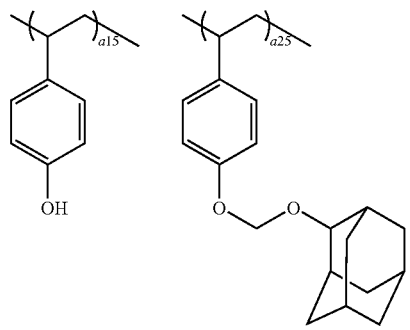

[a15/a25 = 75/25 (molar ratio); Mw = 4200, Mw/Mn = 1.1]

Preparation of Positive Resist Composition-1:
Evaluation as Chemically Amplified Resist Material According to compositions shown in Table 1 Components of Polymers (A)-1 and (A)-2 obtained in Preparation Example 1 and Comparative Preparation Example 1, Component (B) (acid generator), Component (D) (nitrogen-containing organic compound), Component (E) (organic carboxylic acid) and Component (S) (organic solvent) were mixed and dissolved with a predetermined ratio to prepare positive resist compositions of Example 1 and Comparative Example 1.

TABLE 1

|  | Component (A) | Component (B) | Component (D) | Component (E) | Component (S) |
|---|---|---|---|---|---|
| Example 1 | (A)-1 [100] | (B)-1 [12.6] | (D)-1 [0.38] | (E)-1 [0.15] | (S)-1 [3900] |
| Comparative Example 1 | (A)-2 [100] | (B)-1 [12.6] | (D)-1 [0.38] | (E)-1 [0.15] | (S)-1 [3900] |

* Numbers in [ ] in Table represent mixing amounts (parts by mass).
* Components of (B) to (S) are shown below.
(B)-1: Triphenylsulfonium nonafluoro-n-butane sulfonate
(D)-1: Tri-n-octylamine
(E)-1: Salicylic acid
(S)-1: PGMEA <Formation of Resist Pattern-1>

[Sensitivity and Resolution]

Resolutions were evaluated by using the obtained positive resist compositions.

The positive resist composition of each Example was uniformly applied by using a spinner on a silicon substrate with a size of 8 inches treated with hexamethyldisilazane (HMDS) at 90° C. for 36 seconds, and the coated substrate was baked at a temperature shown in Table 2 for 60 seconds (PAB) to form a resist film (a film thickness of 80 nm).

With respect to the resist film, a pattern was drawn (exposed) with an electron beam lithography system HL-800D (VSB) (manufactured by Hitachi, Ltd.) at an acceleration voltage of 70 kV, the film was baked at a temperature shown in Table 2 for 60 seconds (PEB), then developed at 23° C. with a 2.38% by mass aqueous solution of tetramethylammonium hydroxide (TMAH) (trade name: NMD-3, manufactured by Tokyo Ohka Kogyo Co., Ltd.) for 30 seconds, and then rinsed with pure water for 15 seconds to form a line and space (L/S) pattern.

At this time, each optimum exposure amount (Eop; μC/cm$^2$) at which a 100 nm of L/S pattern with a ratio of 1:1 was formed was determined. The results are shown in Table 2.

Each limiting resolution (nm) at the Eop was determined by using a scanning electron microscope S-9220 (manufactured by Hitachi, Ltd.). The results are shown in Table 2 as "resolution (nm)".

TABLE 2

|  | PAB (° C.) | PEB (° C.) | Eop (μC/cm$^2$) | Resolution (nm) |
|---|---|---|---|---|
| Example 1 | 110 | 100 | 44.0 | 60 |
| Comparative Example 1 | 110 | 100 | 24.0 | 70 |

The result of Table 2 shows that the positive resist composition of Example 1 containing the polymer obtained from the coupling agent for anionic polymerization of the present invention as a base resin is superior in the resolution as compared with the positive resist composition of Comparative Example 1.

Furthermore, the resist pattern formed by using the positive resist composition of Example 1 had a fine shape with small roughness.

Preparation Example 2

Preparation of Star Polymers (Polymers (A)-3 to (A)-11)

Preparation Examples 2-1 to 2-2

Synthesis of Arm Part (Polymer Chain) and Synthesis of Acid-Degradable Polymer

Each acid-degradable polymer with a varied molecular weight of polymer chain (PEES polymer) as shown in Table 3 was obtained in the same manner as in Preparation Example 1-2 except that the amount of PEES added was changed as shown in Table 3.

TABLE 3

|  | Amount of PEES Added | Polymer Chain (PEES Polymer) Mn | Polymer Chain (PEES Polymer) Mw/Mn | Acid-Degradable Polymer Mn | Acid-Degradable Polymer Mw/Mn |
|---|---|---|---|---|---|
| Preparation Example 2-1 | 16.3 g | 990 | 1.22 | 3000 | 1.26 |
| Preparation Example 2-2 | 32.8 g | 1860 | 1.10 | 4100 | 1.34 |

* Each value of Mn and Mw/Mn is a value as converted to polystyrene.

Preparation Examples 2-3 to 2-4

Hydrolysis of PEES (Removal of Protective Group)

Each star polymer with PHS segments as a main skeleton of the arm part shown in Table 4 was obtained in the same method as in Preparation Example 1-3 except that the polymer solution obtained in Preparation Example 2-1 or Preparation Example 2-2 was used instead of the polymer solution obtained in Preparation Example 1-2.

TABLE 4

| Star Polymer No. | Polymer Solution Used | Star Polymer Mn | Star Polymer Mw/Mn |
|---|---|---|---|
| Preparation Example 2-3 | Preparation Example 2-1 | 1,830 | 1.29 |
| Preparation Example 2-4 | Preparation Example 2-2 | 2,660 | 1.31 |

* Each value of Mn and Mw/Mn is a value as converted to polystyrene.

Preparation Examples 2-5 to 2-13

Introduction of Acetoxymethyladamantyl Group

MIBK was added to each of the polymer solutions obtained in Preparation Example 1-3, Preparation Example 2-3 and Preparation Example 2-4 and the organic phase was washed with ion-exchanged water three times. Then, the organic phase was concentrated under reduced pressure to make a solution with a polymer content of 50% by mass and then acetone was added to make a solution with a polymer content of 10% by mass.

To 50.0 g of the obtained polymer solution 3.5 g of potassium carbonate was added and the whole was held at room temperature for 30 minutes with stirring. Then, iodoacetoxymethyladamantane was added with an amount shown in Table 5 and the reaction was further continued at 35° C. for 8 hours.

TABLE 5

| | Star Polymer Used | Amount of Iodoacetoxymethyladamantane |
|---|---|---|
| Preparation Example 2-5 | Preparation Example 1-3 | 1.6 g |
| Preparation Example 2-6 | | 2.8 g |
| Preparation Example 2-7 | | 4.0 g |
| Preparation Example 2-8 | Preparation Example 2-3 | 1.6 g |
| Preparation Example 2-9 | | 2.8 g |
| Preparation Example 2-10 | | 3.8 g |
| Preparation Example 2-11 | Preparation Example 2-4 | 1.8 g |
| Preparation Example 2-12 | | 3.0 g |
| Preparation Example 2-13 | | 4.3 g |

To the reaction system, MIBK was added, the organic phase was washed with an aqueous solution of oxalic acid once, and then further washed with ion-exchanged water three times. Then, the organic phase was concentrated under reduced pressure to be replaced with a solution of PGMEA.

$^{13}$C-NMR measurement of the obtained polymer showed novel absorptions around 89 ppm, around 114 ppm and around 169 ppm derived from an unit in which an acetoxymethyladamantyl group was introduced to PHS (hereinafter referred to as PHS-OAdE).

In addition, the ratio of the PHS unit to PHS-OAdE was as shown in Table 6.

Furthermore, it was ascertained that the peak around 96 ppm derived from a —O—CH$_2$—O— bond introduced to the core part of the polymer was held.

Furthermore, GPC measurement of the polymer after the reaction revealed that the polymer was a monodisperse polymer having Mn and Mw/Mn shown in Table 6 and no change was observed in the peak shapes of GPC between before and after the introduction of acetoxymethyladamantyl group.

TABLE 6

| | Polymer | PHS/PHS-OAdE | Mn | Mw/Mn |
|---|---|---|---|---|
| Preparation Example 2-5 | Polymer (A)-3 | 86/14 | 2900 | 1.23 |
| Preparation Example 2-6 | Polymer (A)-4 | 76/24 | 2600 | 1.25 |
| Preparation Example 2-7 | Polymer (A)-5 | 66/34 | 3200 | 1.22 |
| Preparation Example 2-8 | Polymer (A)-6 | 86/14 | 2500 | 1.13 |
| Preparation Example 2-9 | Polymer (A)-7 | 77/23 | 2700 | 1.13 |
| Preparation Example 2-10 | Polymer (A)-8 | 67/33 | 3000 | 1.13 |
| Preparation Example 2-11 | Polymer (A)-9 | 86/14 | 3700 | 1.12 |
| Preparation Example 2-12 | Polymer (A)-10 | 82/18 | 3800 | 1.12 |
| Preparation Example 2-13 | Polymer (A)-11 | 73/27 | 4300 | 1.10 |

* Each value of Mn and Mw/Mn is a value as converted to polystyrene.

From these results, it was ascertained that the alkenylphenolic polymer with PHS/PHS-OAdE segments as a main skeleton of the arm part was obtained, the acetal bonds introduced to the core part of the polymer were held, and the polymer held a star shape.

A structure of each Polymer (A)-3 to Polymer (A)-11 is shown below. In Chemical Formula, each sign at lower right of parentheses shows the ratio of each building block to total building blocks contained in a polymer chain as the arm part of Polymer (A)-3 to Polymer (A)-11 (mol %; composition ratio), and each ratio was calculated from $^{13}$C-NMR and shown in Table 6.

[Chemical Formula 37]

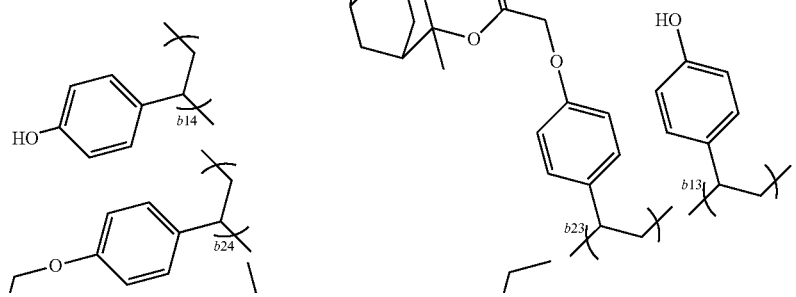

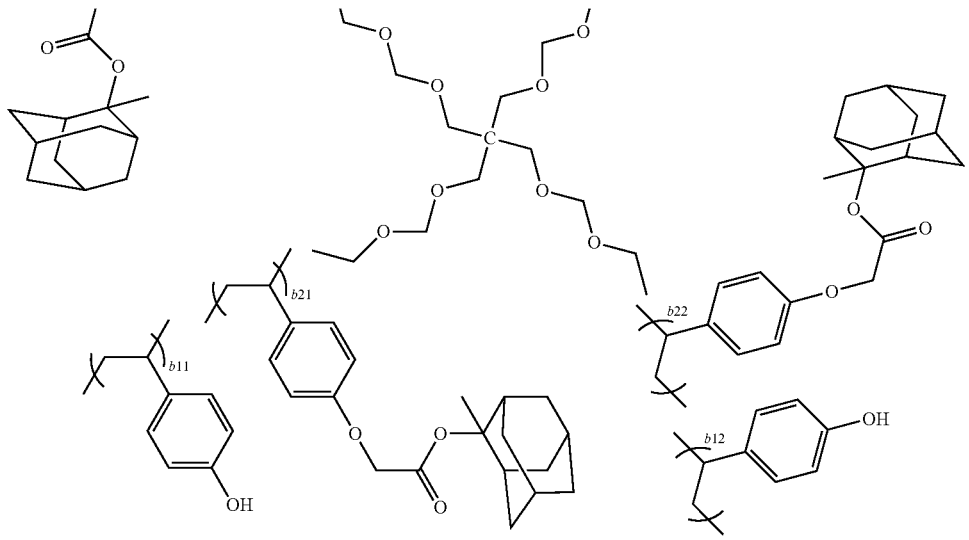

[(b11 + b12 + b13 + b14)/(b21 + b22 + b23 + b24) = the ratio of each building block (molar ratio; see Table 6)]

Comparative Preparation Example 2

Preparation of Polymer (A)-12

5 g of poly-4-hydroxystyrene (Mn=2900, Mw/Mn=1.06) was dissolved in 45 g of acetone, to which 3.5 g of potassium carbonate was added, and the whole was held at room temperature for 30 minutes with stirring. Then, 3.5 g of iodoacetoxymethyladamantane was added and the reaction was further continued at 35° C. for 8 hours.

To the reaction system, MIBK was added, the organic phase was washed with an aqueous solution of oxalic acid once, and then further washed with ion-exchanged water three times. Then, the organic phase was concentrated under reduced pressure to be replaced with a solution of PGMEA.

GPC measurement of the product revealed that Polymer (A)-12 obtained had Mn=4300 and Mw/Mn=1.05 as converted to polystyrene. Furthermore, the composition ratio (molar ratio) was calculated by $^{13}$C-NMR.

A structure of Polymer (A)-12 obtained from Comparative Preparation Example 2 is as shown below.

[Chemical Formula 38]

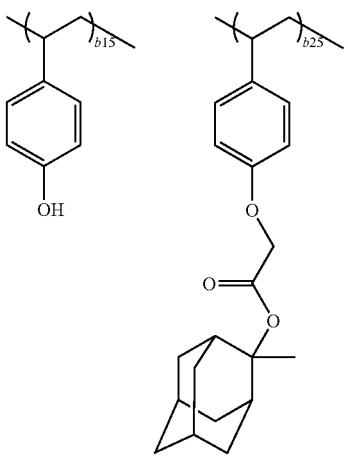

[b15/b25 = 75/25 (molar ratio); Mw = 4300, Mw/Mn = 1.05]

Preparation of Positive Resist Composition-2

Evaluation as Chemically Amplified Resist Material

According to compositions shown in Table 7, Components of Polymers (A)-3 to (A)-11 and (A)-12 obtained in Preparation Example 2 and Comparative Preparation Example 2, Component (B) (acid generator), Component (D) (nitrogen-containing organic compound), Component (E) (organic carboxylic acid) and Component (S) (organic solvent) were mixed and dissolved with a predetermined ratio to prepare positive resist compositions of Examples 2 to 10 and Comparative Example 2.

TABLE 7

|  | Component (A) | Component (B) | Component (D) | Component (E) | Component (S) |
|---|---|---|---|---|---|
| Example 2 | (A)-3 [100] | (B)-2 [37.5] | (D)-1 [1.8] | (E)-1 [0.72] | (S)-2 [3900] |
| Example 3 | (A)-4 [100] | (B)-2 [37.5] | (D)-1 [1.8] | (E)-1 [0.72] | (S)-2 [3900] |
| Example 4 | (A)-5 [100] | (B)-2 [37.5] | (D)-1 [1.8] | (E)-1 [0.72] | (S)-2 [3900] |
| Example 5 | (A)-6 [100] | (B)-2 [37.5] | (D)-1 [1.8] | (E)-1 [0.72] | (S)-2 [3900] |
| Example 6 | (A)-7 [100] | (B)-2 [37.5] | (D)-1 [1.8] | (E)-1 [0.72 | (S)-2 [3900] |
| Example 7 | (A)-8 [100] | (B)-2 [37.5] | (D)-1 [1.8] | (E)-1 [0.72] | (S)-2 [3900] |
| Example 8 | (A)-9 [100] | (B)-2 [37.5] | (D)-1 [1.8] | (E)-1 [0.72] | (S)-2 [3900] |
| Example 9 | (A)-10 [100] | (B)-2 [37.5] | (D)-1 [1.8] | (E)-1 [0.72] | (S)-2 [3900] |
| Example 10 | (A)-11 [100] | (B)-2 [37.5] | (D)-1 [1.8] | (E)-1 [0.72] | (S)-2 [3900] |
| Comparative Example 2 | (A)-12 [100] | (B)-2 [37.5] | (D)-1 [1.8] | (E)-1 [0.72] | (S)-2 [3900] |

* Numbers in [ ] in Table represent mixing amounts (parts by mass).
* Components of (B) to (S) are shown below.
(B)-2: A compound represented by Formula below.

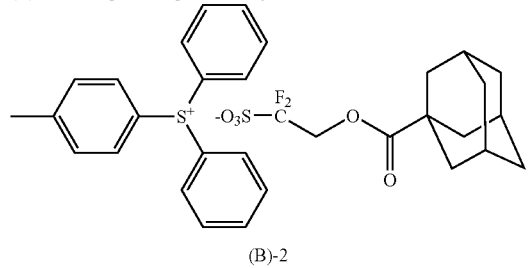

(B)-2

(D)-1: Tri-n-octylamine
(E)-1: Salicylic acid
(S)-2: A mixed solvent of PGMEA/PGME = 6/4 (mass ratio)

<Formation of Resist Pattern-2>
[Evaluation of Sensitivity]

The positive resist composition of each Example was uniformly applied by using a spinner on a silicon substrate with a size of 8 inches treated with hexamethyldisilazane (HMDS) at 90° C. for 36 seconds, and the coated substrate was baked at 100° C. for 60 seconds (PAB) (where only for Example 10, PAB was at 80° C. for 60 seconds) to form a resist film (a film thickness of 80 nm).

With respect to the resist film, a pattern was drawn (exposed) with an electron beam lithography system HL-800D (VSB) (manufactured by Hitachi, Ltd.) at an acceleration voltage of 70 kV, the film was baked at 80° C. for 60 seconds (PEB), then developed at 23° C. with a 2.38% by mass aqueous solution of tetramethylammonium hydroxide (TMAH) (trade name: NMD-3, manufactured by Tokyo Ohka Kogyo Co., Ltd.) for 30 seconds, and then rinsed with pure water for 15 seconds to form a line and space (L/S) pattern. On each of Examples and Comparative Example, the optimum exposure amount (Eop; $\mu C/cm^2$) when a 100 nm of L/S pattern with a ratio of 1:1 was formed was determined. The results are shown in Table 8.

[Evaluation of Line Width Roughness (LWR)]

On a 100 nm of 1:1 L/S pattern formed with the Eop, the line width was measured at five points of the line in the longitudinal direction with a critical dimension scanning electron microscope (SEM, an acceleration voltage of 800V, trade name: S-9220, manufactured by Hitachi, Ltd.). The standard deviation (s) was obtained from the results, and the deviation was tripled as a measure of LWR (3s). A smaller value of 3s means a smaller roughness of a line width, that is, a L/S pattern with a more uniform width was obtained. The results are shown in Table 8.

TABLE 8

|  | Eop ($\mu C/cm^2$) | LWR (nm) |
|---|---|---|
| Example 2 | 42 | 15.5 |
| Example 3 | 44 | 12.3 |
| Example 4 | 42 | 14.6 |
| Example 5 | 52 | 18.6 |
| Example 6 | 54 | 14.0 |
| Example 7 | 48 | 16.7 |
| Example 8 | 50 | 15.2 |
| Example 9 | 54 | 19.0 |
| Example 10 | 44 | 18.5 |
| Comparative Example 2 | 58 | 20.0 |

The result of Table 8 shows that each of the positive resist compositions of Examples 2 to 10 containing the polymer obtained from the coupling agent for anionic polymerization of the present invention as a base resin can give a L/S pattern with a lower LWR value and a uniform width as compared with the positive resist composition of Comparative Example 2.

Preparation of Positive Resist Composition-3

Evaluation as Chemically Amplified Resist Material

According to compositions shown in Table 9, Components of Polymers (A)-6 to (A)-8 and (A)-12 obtained in Preparation Example 2 and Comparative Preparation Example 2, Component (B) (acid generator), Component (D) (nitrogen-containing organic compound), Component (E) (organic carboxylic acid) and Component (S) (organic solvent) were mixed and dissolved with a predetermined ratio to prepare positive resist compositions of Examples 11 to 13 and Comparative Example 3.

TABLE 9

|  | Component (A) | Component (B) | Component (D) | Component (E) | Component (S) |
| --- | --- | --- | --- | --- | --- |
| Example 11 | (A)-6 [100] | (B)-3 [37.5] | (D)-1 [1.8] | (E)-1 [0.72] | (S)-2 [3900] |
| Example 12 | (A)-7 [100] | (B)-3 [37.5] | (D)-1 [1.8] | (E)-1 [0.72] | (S)-2 [3900] |
| Example 13 | (A)-8 [100] | (B)-3 [37.5] | (D)-1 [1.8] | (E)-1 [0.72] | (S)-2 [3900] |
| Compartive Example 3 | (A)-12 [100] | (B)-3 [37.5] | (D)-1 [1.8] | (E)-1 [0.72] | (S)-2 [3900] |

* Numbers in [ ] in Table represent mixing amounts (parts by mass).
* Components of (B) to (S) are shown below.
(B)-3: A compound represented by Formula below.

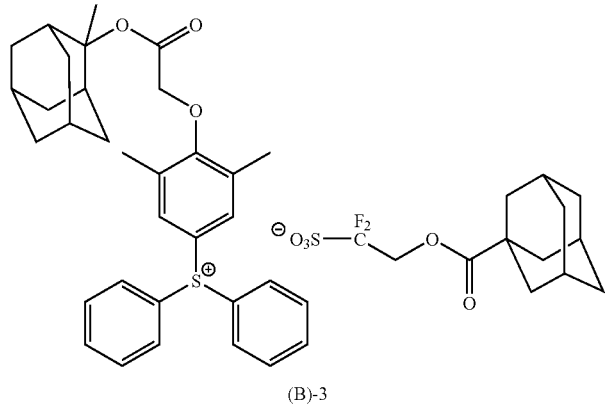

(B)-3

(D)-1: Tri-n-octylamine
(E)-1: Salicylic acid
(S)-2: A mixed solvent of PGMEA/PGME = 6/4 (mass ratio)

TABLE 10

|  | Eop ($\mu C/cm^2$) | LWR (nm) | Resolution (nm) |
| --- | --- | --- | --- |
| Example 11 | 58 | 12.5 | 50 |
| Example 12 | 62 | 11.9 | 50 |
| Example 13 | 58 | 10.7 | 50 |
| Comparative Example 3 | 68 | 16.3 | 60 |

The result of Table 10 shows that each of the positive resist compositions of Examples 11 to 14 containing the polymer obtained from the coupling agent for anionic polymerization of the present invention as a base resin can give a L/S pattern with a lower LWR value, a uniform width and a superior resolution as compared with the positive resist composition of Comparative Example 3.

<Formation of Resist Pattern-3>

A resist pattern was formed with the positive resist composition of each Example in the same manner as in <Formation of Resist Pattern-2>. On each of Examples and Comparative Example, the optimum exposure amount (Eop; $\mu C/cm^2$) when a 100 nm of L/S pattern with a ratio of 1:1 was formed was determined. Furthermore, LWR at the Eop was also evaluated in the same method as in the above.

In addition, each limiting resolution (nm) at the Eop was determined by using a scanning electron microscope S-9220 (manufactured by Hitachi, Ltd.). The obtained results are shown in Table 10.

Preparation Example 3

Preparation of Star Polymer (Polymer (A)-13)

Preparation Example 3-1

Synthesis of Coupling Agent for Anionic Polymerization

Under a nitrogen atmosphere, to 12.3 g of dipentaerythritol 234.1 g of acetone, 50.1 g of diisopropylethylamine and 50.0 g of 2-chloroethyl chloromethyl ether were added and the whole was held at 50° C. for 4 hours with stirring. Then, to the reaction mixture, ethyl acetate was added and the organic phase was washed with an oxalic acid aqueous solution and ion-exchanged water 4 times. The obtained organic phase was concentrated under reduced pressure to obtain 39.0 g of dipentaerythritol-hexa(2-chloroethoxymethyl)ether (yield 99%).

Under a nitrogen atmosphere, to 20.0 g of dipentaerythritol-hexa(2-chloroethoxymethyl)ether obtained above, 480.0 g of hexamethylphosphoric triamide, 161.6 g of bromoethane and 3.1 g of sodium bromide were added and the whole was held at 80° C. for 3 hours with stirring. Then, the reaction mixture was concentrated under reduced pressure. To the obtained concentrated mixture, 107.7 g of bromoethane was newly added and the whole was held at 80° C. for 3 hours with stirring. Then, the reaction mixture was concentrated under reduced pressure, methyl t-butyl ether was added to the obtained concentrated mixture, and the organic phase was washed with ion-exchanged water 4 times. Then, anhydrous magnesium sulfate was added to the organic phase and dried. After filtration, the filtrate was concentrated under reduced pressure to obtain 10.5 g of dipentaerythritol-hexa(2-bromoethoxymethyl)ether (yield 39%) as a coupling agent for anionic polymerization.

Preparation Example 3-2

Synthesis of Arm Part (Polymer Chain) and Synthesis of Acid-Degradable Polymer

Under a nitrogen atmosphere, 263.5 g of THF was cooled to −60° C. With stirring, 30 millimole of s-butyllithium was added while the temperature was held at −60° C., subsequently 42.4 g of PEES was added dropwise over 50 minutes, and then the reaction was continued for 1 hour.

At this stage, a small amount of the reacted solution was taken, methanol was added to stop the reaction, and then the reactant was subjected to GPC measurement to reveal that the obtained PEES polymer was a monodisperse polymer with Mn=1430 and Mw/Mn=1.13 as converted to polystyrene.

Then, to the reaction system with the temperature held at −60° C., 6.6 g of dipentaerythritol-hexa(2-bromoethoxymethyl)ether obtained in Preparation Example 3-1 was added dropwise over 10 minutes and then the reaction was continued for 1 hour.

Then, to the reaction system, methanol was added to stop the reaction. The subsequent GPC measurement revealed that the obtained acid-degradable polymer was a monodisperse polymer with Mn=3620 and Mw/Mn=1.42 as converted to polystyrene.

That is, it was observed that the molecular weight of the polymer increased after the reaction with dipentaerythritol-hexa(2-bromoethoxymethyl)ether while the monodisperse polymer state before the reaction was held. Accordingly, the polymer was ascertained to be a polymer with a star shape.

Preparation Example 3-3

Hydrolysis of PEES (Removal of Protective Group)

To the polymer solution obtained from Preparation Example 3-2, MIBK was added, the organic phase was washed with ion-exchanged water twice, then the organic phase was concentrated under reduced pressure to make a MIBK solution with a polymer content of 40% by mass, and then IPA was added to make a solution with a polymer content of 20% by mass.

With respect to 100 parts by mass of the solution, 1 part by mass of oxalic acid dihydrate and 2 parts by mass of ion-exchanged water were added and the whole was heated to 50° C. With stirring, the reaction was further continued for 8 hours while holding the temperature at 50° C.

$^{13}$C-NMR spectra of the polymers before and after the reaction were measured and the results were compared. After the reaction, the absorption observed around 117 ppm and derived from the PEES polymer disappeared and a novel absorption around 115 ppm derived from the PHS polymer was observed. In addition, the peak observed around 96 ppm and derived from an acetal bond (—O—CH$_2$—O—) was ascertained to be held both before and after the hydrolysis.

Furthermore, GPC measurement of the polymer after the reaction showed Mn=2000 as converted to polystyrene, and no significant change was observed in the peak shapes of GPC between before and after the reaction.

From these results, it was ascertained that hydrolysis at the ethoxyethoxy groups of PEES progressed and an alkenylphenolic polymer with PHS segments as a main skeleton of the arm part was obtained. Furthermore, the —O—CH$_2$—O— bond introduced to the core part of the polymer was held, and the polymer after the reaction held a star shape.

Preparation Example 3-4

Introduction of Acetoxymethyladamantyl Group

To the polymer solution obtained in Preparation Example 3-3, MIBK was added, and the organic phase was washed with ion-exchanged water three times. Then, the organic phase was concentrated under reduced pressure to make a solution with a polymer content of 50% by mass and then acetone was added to make a solution with a polymer content of 10% by mass.

To 50.0 g of the obtained polymer solution, 3.5 g of potassium carbonate was added and the whole was held at room temperature for 30 minutes with stirring. Then, 11.7 g of iodoacetoxymethyladamantane was added and the reaction was further continued at 35° C. for 8 hours.

To the reaction system, MIBK was added, the organic phase was washed with an aqueous solution of oxalic acid once, and then further washed with ion-exchanged water three times. Then, the organic phase was concentrated under reduced pressure to be replaced with a solution of PGMEA.

$^{13}$C-NMR measurement of the obtained polymer showed novel absorptions around 89 ppm, around 114 ppm and around 169 ppm derived from an unit in which an acetoxymethyladamantyl group was introduced to PHS (hereinafter referred to as PHS-OAdE).

In addition, the ratio of the PHS unit to PHS-OAdE was 80/20.

Furthermore, it was ascertained that the peak around 96 ppm derived from an —O—CH$_2$—O— bond introduced to the core part of the polymer was held.

Furthermore, GPC measurement of the polymer after the reaction revealed that the polymer is a monodisperse polymer having Mn=4200 and Mw/Mn=1.34 and no change was observed in the peak shapes of GPC between before and after the introduction of an acetoxymethyladamantyl group.

From these results, it was ascertained that an alkenylphenolic polymer with PHS/PHS-OAdE segments as a main skeleton of the arm part was obtained, the acetal bonds introduced to the core part of the polymer were held, and the polymer held a star shape.

A structure of the polymer obtained in Preparation Example 3-4 (hereinafter, referred to as Polymer (A)-13) is shown below. In Chemical Formula, each sign at lower right of parentheses represents the ratio of each building block to total building blocks contained in a polymer chain as the arm part of Polymer (A)-13 (mol %; composition ratio), and each ratio was calculated from $^{13}$C-NMR.

[Chemical Formula 39]

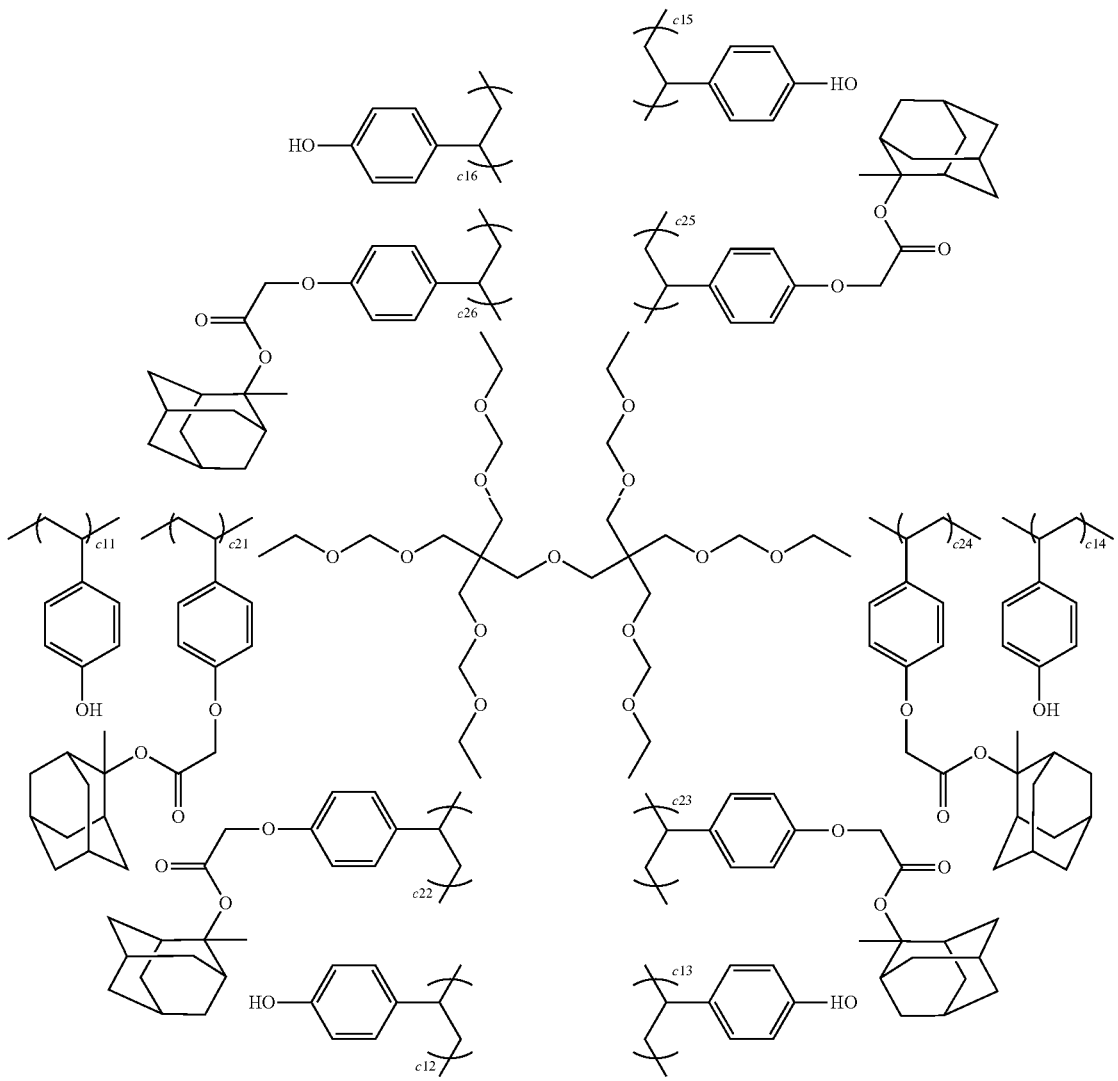

[(c11 + c12 + c13 + c14 + c15 + c16)/(c21 + c22 + c23 + c24 + c25 + c26) = 80/20 (molar ratio); Mw = 4200, Mw/Mn = 1.34]

Preparation of Positive Resist Composition-4

Evaluation as Chemically Amplified Resist Material

According to compositions shown in Table 11, Components of Polymers (A)-7 to (A)-13 obtained in Preparation Example 2 and Preparation Example 3, Component (B) (acid generator), Component (D) (nitrogen-containing organic compound), Component (E) (organic carboxylic acid) and Component (S) (organic solvent) were mixed and dissolved with a predetermined ratio to prepare positive resist compositions of Examples 14 to 16.

TABLE 11

|  | Component (A) | Component (B) | Component (D) | Component (E) | Component (S) |
|---|---|---|---|---|---|
| Example 14 | (A)-7 | (B)-2 | (D)-1 | — | (S)-2 |
|  | [100] | [23.0] | [1.5] |  | [3900] |
| Example 15 | (A)-13 | (B)-2 | (D)-1 | — | (S)-2 |
|  | [100] | [37.5] | [1.8] |  | [3900] |

TABLE 11-continued

|  | Component (A) | Component (B) | Component (D) | Component (E) | Component (S) |
|---|---|---|---|---|---|
| Example 16 | (A)-13 [100] | (B)-3 [37.5] | (D)-1 [1.8] | (E)-1 [0.72] | (S)-2 [3900] |

* Numbers in [ ] in Table represent mixing amounts (parts by mass).
* Components of (B) to (S) are shown below.
(B)-2, (B)-3: Compounds represented by Formulae below.

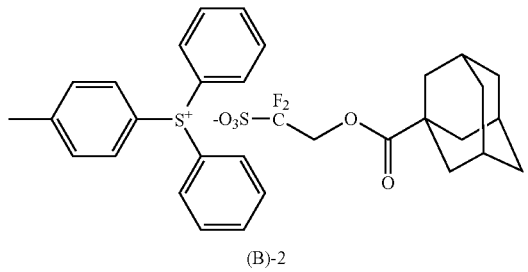

(B)-2

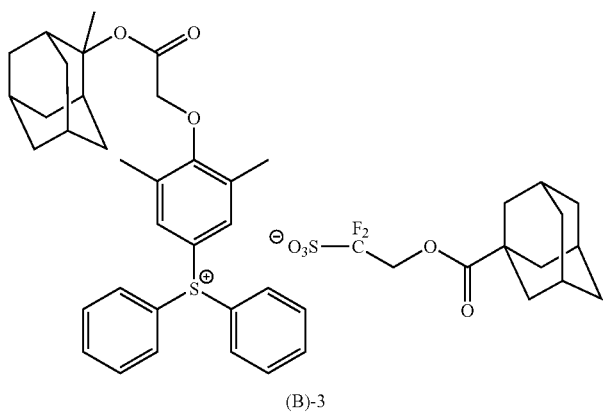

(B)-3

(D)-1: Tri-n-octylamine
(E)-1: Salicylic acid
(S)-2: A mixed solvent of PGMEA/PGME = 6/4 (mass ratio)

<Formation of Resist Pattern-4>

A resist pattern was formed with the positive resist composition of each Example in the same manner as in <Formation of Resist Pattern-2> except that the PAB temperature was changed to 80° C. On each Example, the optimum exposure amount (Eop; μC/cm$^2$) when a 100 nm of L/S pattern with a ratio of 1:1 was formed was determined. Furthermore, the LWR and limiting resolution (nm) at the Eop were evaluated in the same method as in the above.

The obtained results are shown in Table 12.

TABLE 12

|  | Eop (μC/cm$^2$) | LWR (nm) | Resolution (nm) |
|---|---|---|---|
| Example 14 | 42 | 15.6 | 50 |
| Example 15 | 42 | 14.0 | 50 |
| Example 16 | 64 | 13.0 | 50 |

The result of Table 12 shows that each of the positive resist compositions of Examples 14 to 16 containing the polymer obtained from the coupling agent for anionic polymerization of the present invention as a base resin can give a L/S pattern with a low LWR value, a uniform width and a superior resolution.

Preparation Example 4

Preparation of Star Polymer (Polymer (A)-14)

Preparation Example 4-1

Introduction of Adamantyloxyethyl Group

To the polymer solution obtained in Preparation Example 1-3, MIBK was added and the organic phase was washed with ion-exchanged water three times. Then, the organic phase was concentrated under reduced pressure and then PGMEA was added to make a solution with a polymer content of 30% by mass.

To 50.0 g of the obtained polymer solution, 0.7 g of trifluoroacetic acid was added, followed by stirring at 30° C. Then, 9.4 g of adamantyl vinyl ether was added and the reaction was further continued at 30° C. for 3 hours.

To the reaction system triethylamine was added to stop the reaction, then MIBK was added, and the organic phase was washed with ion-exchanged water three times. Then, the organic phase was concentrated under reduced pressure to be replaced with a solution of PGMEA.

$^{13}$C-NMR measurement of the obtained polymer showed novel absorptions around 94 ppm, around 118 ppm and around 156 ppm derived from an unit in which an adamantyloxyethyl group was introduced to PHS (hereinafter referred to as PHS-AdVE).

In addition, the ratio of the PHS unit and PHS-AdVE was 80/20.

Furthermore, it was ascertained that the peak around 96 ppm derived from an —O—$CH_2$—O— bond introduced to the core part of the polymer was held.

Furthermore, GPC measurement of the polymer after the reaction revealed that the polymer is a monodisperse polymer having Mn=3400 and Mw/Mn=1.22 and no change was observed in the peak shapes of GPC between before and after the introduction of an adamantyloxyethyl group.

From these results, it was ascertained that an alkenylphenolic polymer with PHS/PHS-AdVE segments as a main skeleton of the arm part was obtained, the acetal bonds introduced to the core part of the polymer were held, and the polymer held a star shape.

A structure of the polymer obtained in Preparation Example 4-1 (hereinafter, referred to as Polymer (A)-14) is shown below. In Chemical Formula, each sign at lower right of parentheses represents the ratio of each building block to total building blocks contained in a polymer chain as the arm part of Polymer (A)-14 (mol %; composition ratio), and each ratio was calculated from $^{13}$C-NMR.

[Chemical Formula 40]

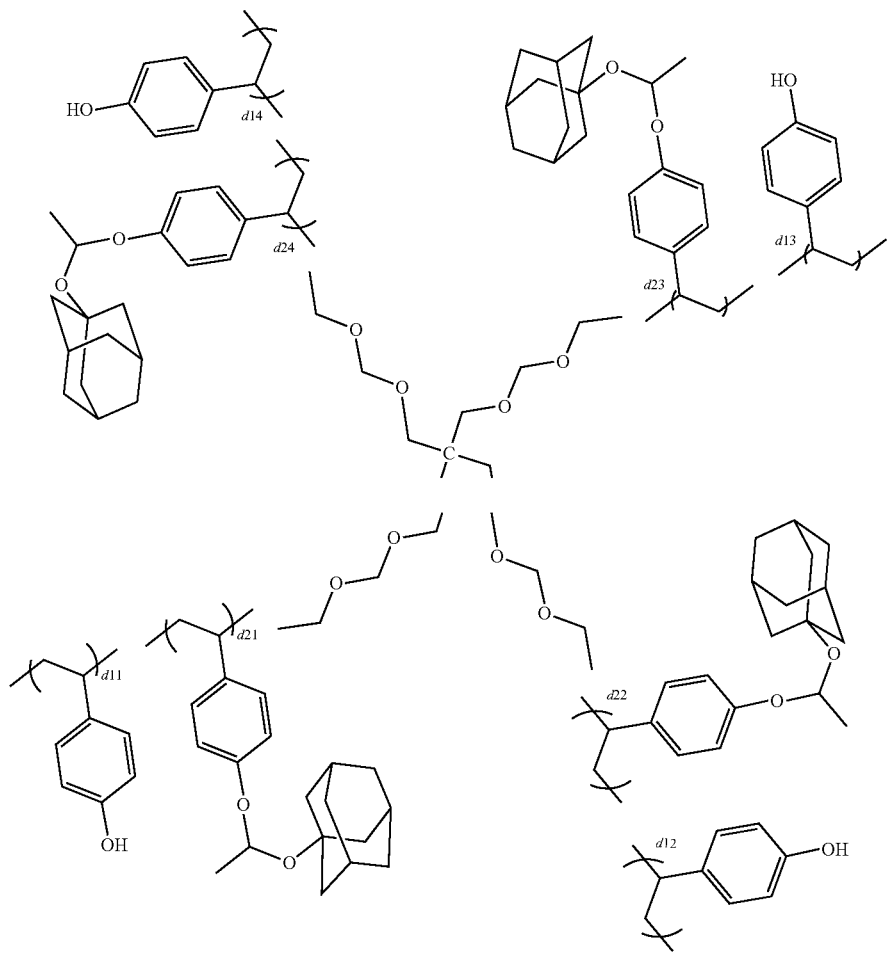

[(d11 + d12 + d13 + d14)/(d21 + d22 + d23 + d24) = 80/20 (molar ratio); Mw = 3400, Mw/Mn = 1.22]

Preparation of Positive Resist Composition-5

Evaluation as Chemically Amplified Resist Material

According to compositions shown in Table 13, Component of Polymer (A)-14 obtained in Preparation Example 4, Component (B) (acid generator), Component (D) (nitrogen-containing organic compound), Component (E) (organic carboxylic acid) and Component (S) (organic solvent) were mixed and dissolved with a predetermined ratio to prepare positive resist compositions of Examples 17 and 18.

TABLE 13

| | Component (A) | Component (B) | Component (D) | Component (E) | Component (S) |
|---|---|---|---|---|---|
| Example 17 | (A)-14 [100] | (B)-2 [23.0] | (D)-1 [1.5] | — | (S)-2 [3900] |
| Example 18 | (A)-14 [100] | (B)-3 [37.5] | (D)-1 [1.8] | (E)-1 [0.72] | (S)-2 [3900] |

\* Numbers in [ ] in Table represent mixing amounts (parts by mass).
\* Components of (B) to (S) are shown below.
(B)-2, (B)-3: Compounds represented by Formulae below.

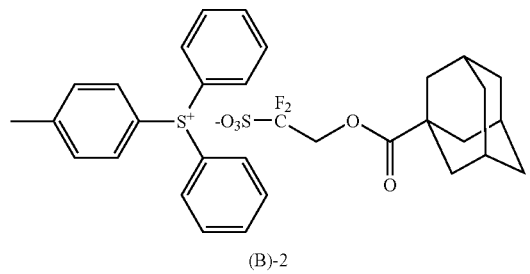

(B)-2

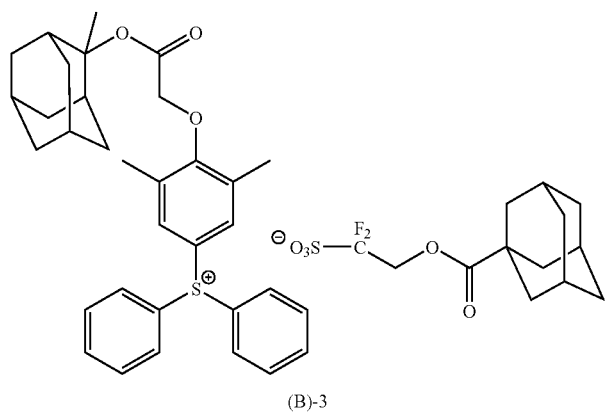

(B)-3

(D)-1: Tri-n-octylamine
(E)-1: Salicylic acid
(S)-2: A mixed solvent of PGMEA/PGME = 6/4 (mass ratio)

<Formation of Resist Pattern-5>

A resist pattern was formed with the positive resist composition of each Example in the same manner as in <Formation of Resist Pattern-2> except that the PAB temperature was changed to 80° C. On each Example, the optimum exposure amount (Eop; µC/cm$^2$) when a 100 nm of L/S pattern with a ratio of 1:1 was formed was determined. Furthermore, the LWR and limiting resolution (nm) at the Eop were evaluated in the same method as in the above.

The obtained results are shown in Table 14.

TABLE 14

| | Eop (µC/cm$^2$) | LWR (nm) | Resolution (nm) |
|---|---|---|---|
| Example 17 | 20 | 19.0 | 50 |
| Example 18 | 40 | 14.5 | 60 |

The result of Table 14 shows that each of the positive resist compositions of Examples 17 to 18 containing the polymer obtained from the coupling agent for anionic polymerization of the present invention as a base resin can give a L/S pattern with a low LWR value, a uniform width and a superior resolution.

Preparation Example 5

Preparation of Star Polymers (Polymers (A)-15 to (A)-20)

Preparation Examples 5-1 to 5-2

Synthesis of Arm Part (Polymer Chain) and Synthesis of Acid-Degradable Polymer

Each acid-degradable polymer with a varied molecular weight of polymer chain (PEES polymer) shown in Table 15 was obtained in the same manner as in Preparation Example 3-2 except that the amount of PEES added was changed as shown in Table 15 and a water content during the reaction was reduced by using a glove box or the like.

TABLE 15

|  | Amount of PEES Added | Polymer Chain (PEES Polymer) Mn | Polymer Chain (PEES Polymer) Mw/Mn | Acid-Degradable Polymer Mn | Acid-Degradable Polymer Mw/Mn |
| --- | --- | --- | --- | --- | --- |
| Preparation Example 5-1 | 42.4 g | 1460 | 1.15 | 4800 | 1.19 |
| Preparation Example 5-2 | 29.0 g | 960 | 1.38 | 4000 | 1.20 |

* Each value of Mn and Mw/Mn is a value as converted to polystyrene.

Preparation Examples 5-3 to 5-4

Hydrolysis of PEES (Removal of Protective Group)

Each star polymer with PHS segments shown in Table 16 as a main skeleton of the arm part was obtained in the same method as in Preparation Example 3-3 except that the polymer solution obtained in Preparation Example 5-1 or Preparation Example 5-2 was used instead of the polymer solution obtained in Preparation Example 3-2.

TABLE 16

| Star Polymer No. | Polymer Solution Used | Star Polymer Mn | Star Polymer Mw/Mn |
| --- | --- | --- | --- |
| Preparation Example 5-3 | Preparation Example 5-1 | 2900 | 1.12 |
| Preparation Example 5-4 | Preparation Example 5-2 | 2070 | 1.37 |

* Each value of Mn and Mw/Mn is a value as converted to polystyrene

Preparation Examples 5-5 to 5-10

Introduction of Acetoxymethyladamantyl Group

Each alkenylphenolic star polymer with PHS/PHS-OAdE segments shown in Table 18 as a main skeleton of the arm part was obtained in the same method as in Preparation Example 3-4 except that the polymer solution obtained in Preparation Example 5-3 or Preparation Example 5-4 was used instead of the polymer solution obtained in Preparation Example 3-3 and the addition amount of iodoacetoxymethyladamantane was changed as shown in Table 17.

TABLE 17

|  | Star Polymer Used | Amount of Iodoacetoxymethyladamantane Added |
| --- | --- | --- |
| Preparation Example 5-5 | Preparation Example 5-3 | 1.8 g |
| Preparation Example 5-6 |  | 3.0 g |
| Preparation Example 5-7 |  | 4.2 g |
| Preparation Example 5-8 | Preparation Example 5-4 | 1.7 g |
| Preparation Example 5-9 |  | 2.8 g |
| Preparation Example 5-10 |  | 3.9 g |

TABLE 18

|  | Polymer | PHS/PHS-OAdE | Mn | Mw/Mn |
| --- | --- | --- | --- | --- |
| Preparation Example 5-5 | Polymer (A)-15 | 84/16 | 4180 | 1.13 |
| Preparation Example 5-6 | Polymer (A)-16 | 74/26 | 4630 | 1.12 |
| Preparation Example 5-7 | Polymer (A)-17 | 64/36 | 5180 | 1.06 |
| Preparation Example 5-8 | Polymer (A)-18 | 84/16 | 3440 | 1.10 |
| Preparation Example 5-9 | Polymer (A)-19 | 75/25 | 3950 | 1.09 |
| Preparation Example 5-10 | Polymer (A)-20 | 65/35 | 4300 | 1.09 |

* Each value of Mn and Mw/Mn is a value as converted to polystyrene.

Preparation of Positive Resist Composition-6

Evaluation as Chemically Amplified Resist Material

According to compositions shown in Table 19, Components of Polymers (A)-15 to (A)-20 obtained in Preparation Example 5, Component (B) (acid generator), Component (D) (nitrogen-containing organic compound), Component (E) (organic carboxylic acid) and Component (S) (organic solvent) were mixed and dissolved with a predetermined ratio to prepare positive resist compositions of Examples 19 to 24.

TABLE 19

|  | Component (A) | Component (B) | Component (D) | Component (E) | Component (S) |
| --- | --- | --- | --- | --- | --- |
| Example 19 | (A)-15 | (B)-3 | (D)-1 | (E)-1 | (S)-2 |
|  | [100] | [37.5] | [1.4] | [0.56] | [3900] |
| Example 20 | (A)-16 | (B)-3 | (D)-1 | (E)-1 | (S)-2 |
|  | [100] | [37.5] | [1.4] | [0.56] | [3900] |
| Example 21 | (A)-17 | (B)-3 | (D)-1 | (E)-1 | (S)-2 |
|  | [100] | [37.5] | [1.4] | [0.56] | [3900] |
| Example 22 | (A)-18 | (B)-3 | (D)-1 | (E)-1 | (S)-2 |
|  | [100] | [37.5] | [1.4] | [0.56] | [3900] |
| Example 23 | (A)-19 | (B)-3 | (D)-1 | (E)-1 | (S)-2 |
|  | [100] | [37.5] | [1.4] | [0.56] | [3900] |

TABLE 19-continued

|  | Component (A) | Component (B) | Component (D) | Component (E) | Component (S) |
|---|---|---|---|---|---|
| Example 24 | (A)-20 [100] | (B)-3 [37.5] | (D)-1 [1.4] | (E)-1 [0.56] | (S)-2 [3900] |

* Numbers in [ ] in Table represent mixing amounts (parts by mass).
* Components of (B) to (S) are shown below.

(B)-3: A compound represented by Formula below.

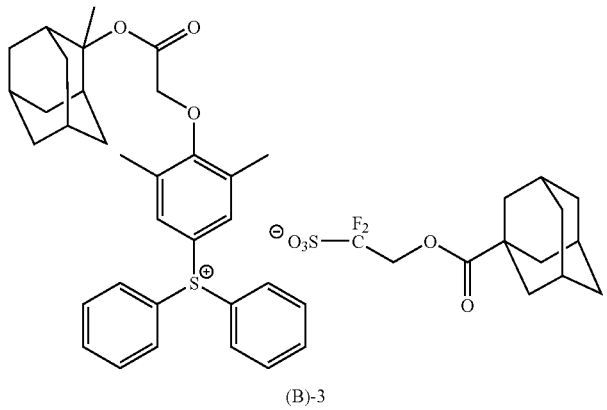

(B)-3

(D)-1: Tri-n-octylamine
(E)-1: Salicylic acid
(S)-2: A mixed solvent of PGMEA/PGME = 6/4 (mass ratio)

<Formation of Resist Pattern-6>
[Sensitivity, LWR and Limiting Resolution]

A resist pattern was formed with the positive resist composition of each Example in the same manner as in <Formation of Resist Pattern-2> except that the PAB temperature was changed to 90° C. and the film thickness of the resist film was 50 nm.

With respect to the resist film, a pattern was drawn (exposed) with an electron beam lithography system HL-800D (VSB) (manufactured by Hitachi, Ltd.) at an acceleration voltage of 70 kV, the film was baked at 80° C. for 60 seconds (PEB), then developed at 23° C. with a 2.38% by mass aqueous solution of tetramethylammonium hydroxide (TMAH) (trade name: NMD-3, manufactured by Tokyo Ohka Kogyo Co., Ltd.) for 60 seconds, and then rinsed with pure water for 15 seconds to form a line and space (L/S) pattern.

On each Example, the optimum exposure amount (Eop; µC/cm$^2$) when a 100 nm of L/S pattern with a ratio of 1:1 was formed was determined by the method described above. Furthermore, the LWR and limiting resolution (nm) at the Eop were evaluated in the same method as in the above.

The obtained results are shown in Table 20.

TABLE 20

|  | Eop (µC/cm$^2$) | LWR (nm) | Limiting Resolution (nm) |
|---|---|---|---|
| Example 19 | 50 | 14.7 | 50 |
| Example 20 | 48 | 12.5 | 50 |
| Example 21 | 38 | 12.0 | 50 |
| Example 22 | 38 | 12.7 | 50 |
| Example 23 | 36 | 10.8 | 50 |
| Example 24 | 34 | 10.4 | 50 |

The result of Table 20 shows that each of the positive resist compositions of Example 19 to Example 24 containing the polymer obtained from the coupling agent for anionic polymerization of the present invention as a base resin can give a L/S pattern with a low LWR value, a uniform width and a superior resolution.

Related Art Documents

[Patent Documents]
[Patent Document 1] Japanese Patent Application Publication No. JP-A-2002-226513
[Patent Document 2] Japanese Patent Application Publication No. JP-A-2006-225605

The invention claimed is:
1. A star polymer comprising:
a core part derived from a coupling agent for anionic polymerization represented by Formula (1):
[Chemical Formula 1]

$$P-(-X-Y-Z)_a \quad (1)$$

where P represents an a-valent organic group, a represents 2 to 20, X represents a linking group capable of being cleaved by acid and represented by Formulae (2) to (4):

[Chemical Formula 2]

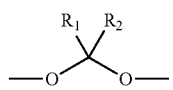 (2)

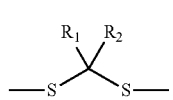 (3)

-continued

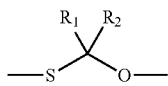

(4)

where each of $R_1$, $R_2$, $R_3$ and $R_4$ independently represents a hydrogen atom; or straight chain, branched or cyclic alkyl group or alkoxy group with 1 to 12 carbon atoms capable of being substituted with an alkoxy group, hydroxy group, halogen atom or epoxy group; aryl group or hydroxy group; and $R_5$ represents a direct bond or straight chain, branched or cyclic alkylene group with 1 to 12 carbon atoms capable of being substituted with an alkoxy group, hydroxy group, halogen atom or epoxy group, or arylene group), Y represents an alkylene group with 1 to 12 carbon atoms or arylene group, and Z represents a halogen atom or epoxy group represented by Formula (6):

[Chemical Formula 3]

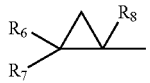

(6)

where each of $R_6$, $R_7$ and $R_8$ independently represents a hydrogen atom or alkyl group with 1 to 12 carbon atoms; and an arm part having a polymer chain obtained by anionic polymerization, the arm part being attached to the core part.

2. The star polymer according to claim 1, characterized in that if Z is a bromine atom in Formula (1), Y bonded to Z represents an alkylene group with 1 to 4 carbon atoms.

3. The star polymer according to claim 1, characterized in that the arm part containing the polymer chain obtained by anionic polymerization includes a repeating unit having hydroxystyrene or a derivative thereof.

4. The star polymer according to claim 1, characterized in that the arm part containing the polymer chain obtained by anionic polymerization includes a repeating unit having an acid-cleavable group.

5. The star polymer according to claim 4, characterized in that the acid-cleavable group is an acetal-type acid-cleavable group represented by General Formula (p 1):

[Chemical Formula 4]

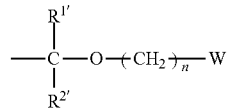

(p1)

where each of $R^{1'}$ and $R^{2'}$ independently represents a hydrogen atom or alkyl group with 1 to 5 carbon atoms, n represents an integer of 0 to 3, and W represents an alicyclic group or alkyl group with 1 to 5 carbon atoms.

* * * * *